United States Patent
Thompson et al.

(10) Patent No.: US 7,338,722 B2
(45) Date of Patent: Mar. 4, 2008

(54) PHENYL AND FLUORENYL SUBSTITUTED PHENYL-PYRAZOLE COMPLEXES OF IR

(75) Inventors: Mark E. Thompson, Anaheim, CA (US); Arnold Tamayo, Glendale, CA (US); Peter Djurovich, Los Angeles, CA (US)

(73) Assignee: The University of Southern California, Los Angeles, CA (US)

( * ) Notice: Subject to any disclaimer, the term of this patent is extended or adjusted under 35 U.S.C. 154(b) by 331 days.

(21) Appl. No.: 10/807,738

(22) Filed: Mar. 24, 2004

(65) Prior Publication Data

US 2004/0253478 A1 Dec. 16, 2004

Related U.S. Application Data

(60) Provisional application No. 60/457,012, filed on Mar. 24, 2003.

(51) Int. Cl.
*H01L 51/54* (2006.01)
*C09K 11/06* (2006.01)

(52) U.S. Cl. ............ 428/690; 428/917; 313/504; 313/506; 257/E51.044; 548/101; 548/103

(58) Field of Classification Search ............ None
See application file for complete search history.

(56) References Cited

U.S. PATENT DOCUMENTS 4,769,292 A 9/1988 Tang et al.

(Continued)

FOREIGN PATENT DOCUMENTS

| JP | 2002 105055 | 4/2002 |
|---|---|---|
| WO | WO 01/41512 | 6/2001 |
| WO | WO 02/15645 | 2/2002 |
| WO | WO 02/074015 | 9/2002 |

OTHER PUBLICATIONS

Dedeian et al., "Photophysical and Electrochemical Properties of Heteroleptic Tris-Cyclometalated Iridium (III) Complexes", Inorganic Chemistry, 44(13), pp. 4445-4447, published on Web May 21, 2005.*

(Continued)

*Primary Examiner*—Marie Yamnitzky
(74) *Attorney, Agent, or Firm*—Kenyon & Kenyon LLP

(57) ABSTRACT

An organic light emitting device is provided, having an anode, a cathode, and an emissive layer disposed between the anode and the cathode. The emissive layer may include the following compound:

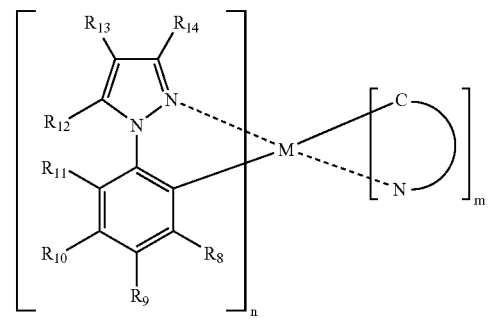

wherein
M is a metal having an atomic weight greater than 40;
(C—N) is a substituted or unsubstituted cyclometallated ligand, and (C—N) is different from at least one other ligand attached to the metal;
each R is independently selected from hydrogen, alkyl, alkenyl, alkynyl, alkylaryl, CN, $CF_3$, $CO_2R$, C(O)R, $NR_2$, $NO_2$, OR, halo, aryl, heteroaryl, substituted aryl, substituted heteroaryl, or a heterocyclic group.

The emissive layer may also include a compound having a metal bonded to at least two ligands, in which one ligand has a triplet energy corresponding to a wavelength that is at least 80 nm greater than the wavelength corresponding to the triplet energy of other ligands. Each ligand may be organometallic.

55 Claims, 5 Drawing Sheets

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,310,360 B1 | 10/2001 | Forrest et al. |
| 6,337,102 B1 | 1/2002 | Forrest et al. |
| 6,468,819 B1 | 10/2002 | Kim et al. |
| 2001/0019782 A1 | 9/2001 | Igarashi et al. |
| 2002/0034656 A1 | 3/2002 | Thompson et al. |
| 2002/0182441 A1 | 12/2002 | Lamansky et al. |
| 2003/0072964 A1 | 4/2003 | Kwong et al. |
| 2003/0124381 A1 | 7/2003 | Thompson et al. |
| 2003/0175553 A1 | 9/2003 | Thompson et al. |
| 2003/0230980 A1 | 12/2003 | Forrest et al. |
| 2004/0048101 A1 | 3/2004 | Thompson et al. |
| 2004/0086743 A1 | 5/2004 | Brown et al. |
| 2004/0174116 A1 | 9/2004 | Lu et al. |

OTHER PUBLICATIONS

Kwong et al., "High Operational Stability of Electrophosphorescent Devices," Appl. Phys. Lett., vol. 81, No. 1, pp. 162-164 (2002).

Baldo et al., "Highly Efficient Phosphorescent Emission from Organic Electroluminescent Devices," Nature, vol. 395, pp. 151-154 (1998).

Baldo et al., "Very High-Efficiency Green Organic Light-Emitting Devices Based on Electrophosphorescence," Appl. Phys. Lett., vol. 75, No. 1, 4-6 (1999).

Adachi et al., "Nearly 100% Internal Phosphorescent Efficiency in an Organic Light Emitting Device," J. Appl. Phys., vol. 90, No. 10, pp. 5048-5051 (2001).

V. Adamovich, et al., "High Efficiency single dopant white electrophosphorescent light emitting diodes", New J. Chem., 2002, 26, pp. 1171-1178.

* cited by examiner

US 7,338,722 B2

PHENYL AND FLUORENYL SUBSTITUTED PHENYL-PYRAZOLE COMPLEXES OF IR

This application is related to and claims priority from U.S. Provisional Patent Application 60/457,012, filed Mar. 24, 2003, which is incorporated by reference in its entirety.

RESEARCH AGREEMENTS

The claimed invention was made by, on behalf of, and/or in connection with one or more of the following parties to a joint university-corporation research agreement: Princeton University, The University of Southern California, and Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and more specifically to phosphorescent organic materials used in such devices. More specifically, the present invention relates to phosphorescent materials with improved electroluminescent efficiencies when incorporated into an OLED.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be an fluorescent or phosphorescent small molecule emitter. A dendrimer may be a "small molecule," and it is believed that all dendrimers currently used in the field of OLEDs are small molecules.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

Industry standards call for the lifetime of such full color displays to be at least about 5000 hours. In addition, high stability and efficiency are important characteristics of high quality displays. These requirements have helped generate a need for phosphorescent emissive materials that exhibit longer lifetimes, higher stability, and higher efficiency in the red, green and blue wavelength regimes than have been achieved in the prior art.

One example of a green emissive molecule is tris(2-phenylpyridine)iridium, denoted Ir(ppy)$_3$, which has following structure:

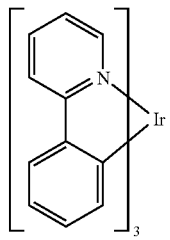

In this, and later figures herein, we depict the dative bond from nitrogen to metal (here, Ir) as a straight line. Ir(ppy)$_3$ emits a spectrum at CIE 0.30, 0.63, and has a halflife of about 10,000 hours at an initial luminance of 500 cd/m$^2$, and a quantum efficiency of about 6%. Kwong et al., *Appl. Phys. Lett.*, 81, 162 (2002).

SUMMARY OF THE INVENTION

An organic light emitting device is provided. The device has an anode, a cathode, and an emissive layer disposed between and electrically connected to the anode and the cathode. The emissive layer may further include a compound with the following structure:

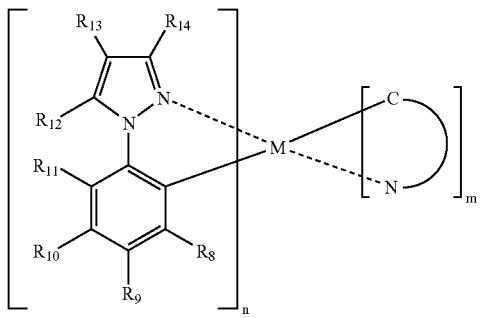

wherein
M is a metal having an atomic weight greater than 40;
(C—N) is a substituted or unsubstituted cyclometallated ligand, and (C—N) is different from at least one other ligand attached to the metal;
each of $R_8$ through $R_{14}$ is independently selected from hydrogen, alkyl, alkenyl, alkynyl, alkylaryl, CN, CF$_3$, CO$_2$R, C(O)R, NR$_2$, NO$_2$, OR, halo, aryl, heteroaryl, substituted aryl, substituted heteroaryl, or a heterocyclic group, wherein each R is independently selected from the group consisting of H, alkyl, alkaryl, and aryl;
additionally or alternatively, any two adjacent substituted positions together form, independently, a fused 4- to 7-member cyclic group, wherein said cyclic group is cycloalkyl, cycloheteroalkyl, aryl, or heteroaryl, and wherein the 4- to 7-member cyclic group may be optionally substituted with substituent R;
m may have a value of at least 1;
n has a value of at least 1; and where n is 3, R is not a cyano group;
m+n is the maximum number of ligands that may be attached to the metal.

The emissive layer may further include a compound comprising a metal bonded to at least a first ligand and a second ligand, in which the first ligand has a triplet energy corresponding to a wavelength that is at least 80 nm greater than the wavelength corresponding to the triplet energy of other ligands. The compound may have only one first ligand bound to the metal. Each ligand may be organometallic.

The emissive material may have enhanced electroluminescent efficiency and improved lifetime when incorporated into a light emitting device.

DETAILED DESCRIPTION

Figure 1:
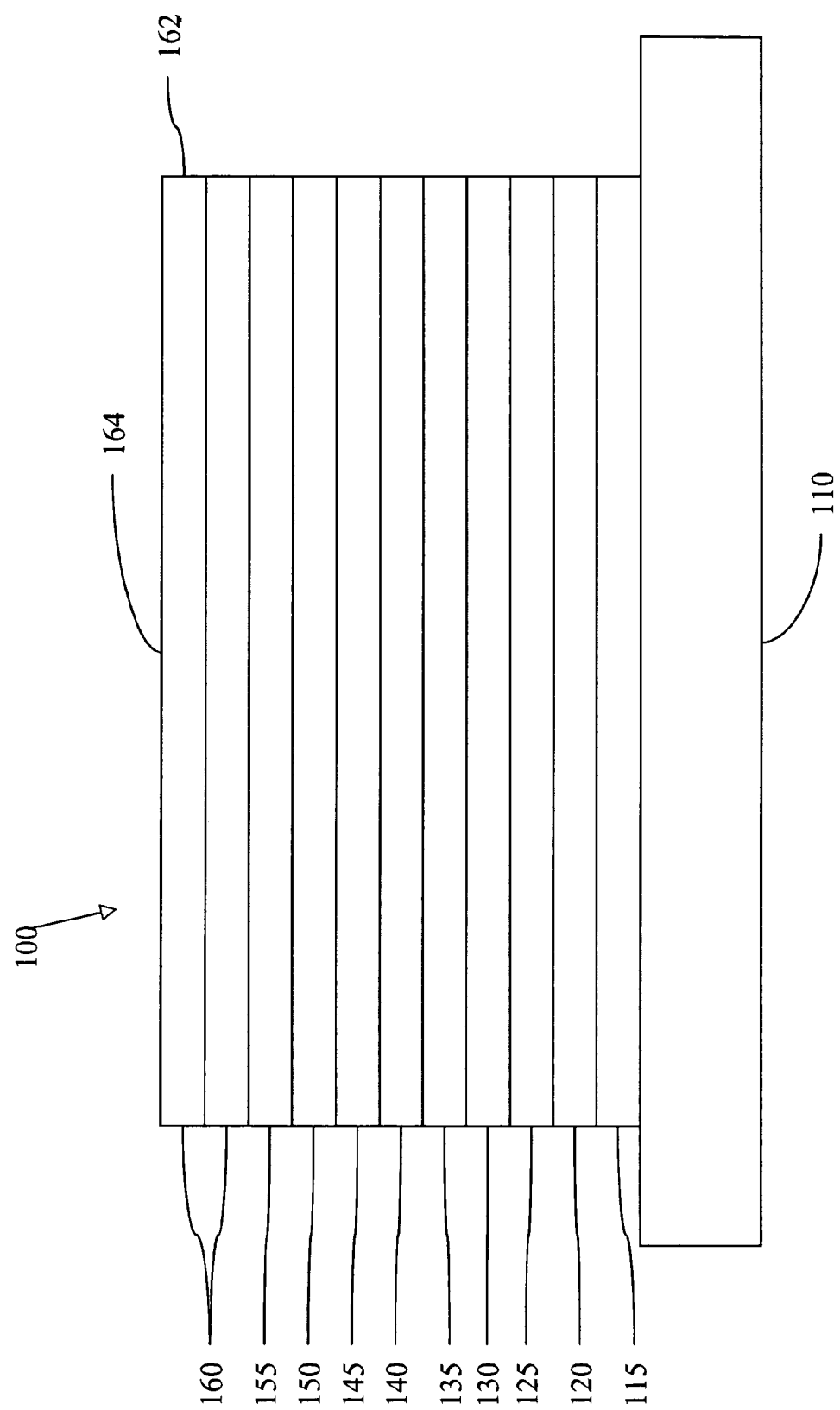
FIG. 1 shows an organic light emitting device having separate electron transport, hole transport, and emissive layers, as well as other layers.

Generally, an OLED comprises at least one organic layer disposed between and electrically connected to an anode and a cathode. As used herein, the term "disposed between and electrically connected to" does not indicate that the recited layers are necessarily adjacent and in direct contact. Rather, it allows for the disposition of additional layers between the recited layers. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a nonradiative mechanism, such that no light is emitted. Organic phosphorescence is also often observed in molecules containing heteroatoms with unshared pairs of electrons at very low temperatures. 2,2'-bipyridine is such a molecule. Nonradiative decay mechanisms are typically temperature dependent, such that a material that exhibits phosphorescence at liquid nitrogen temperatures may not exhibit phosphorescence at room temperature. But, as demonstrated by Baldo, this problem may be addressed by selecting phosphorescent compounds that do phosphoresce at room temperature. Representative emissive layers include doped or un-doped phosphorescent organo-metallic materials such as disclosed in U.S. Pat. Nos. 6,303,238 and 6,310,360; U.S. Patent Application Publication Nos. 2002-0034656; 2002-0182441; and 2003-0072964; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. No. 5,844,363, which is incorporated by reference in its entirety. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003/023980, which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include Ir(ppy)$_3$. Examples of fluorescent emissive materials include DCM and DMQA. Examples of host materials include Alq$_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. Other emissive layer materials and structures may be used.

Electron transport layer 140 may include a material capable of transporting electrons. Electron transport layer 140 may be intrinsic (undoped), or doped. Doping may be used to enhance conductivity. Alq$_3$ is an example of an intrinsic electron transport layer. An example of an n-doped electron transport layer is BPhen doped with Li at a molar ratio of 1:1, as disclosed in United States Patent Application Publication No. 2003/0230980, which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) level of the electron transport layer. The "charge carrying component" is the material responsible for the LUMO that actually transports electrons. This component may be the base material, or it may be a dopant. The LUMO level of an organic material may be generally characterized by the electron affinity of that material and the relative electron injection efficiently of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 35 and electron transport layer 145, to block holes from leaving emissive layer 135 in the direction of electron transport layer 140. Blocking layers may also be used to block excitons from diffusing out of the emissive layer. The theory and use of blocking layers is described in more detail in U.S. Pat. No. 6,097,147 and United States Patent Application Publication No. 2003/0230980, which are incorporated by reference in their entireties.

As used herein, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
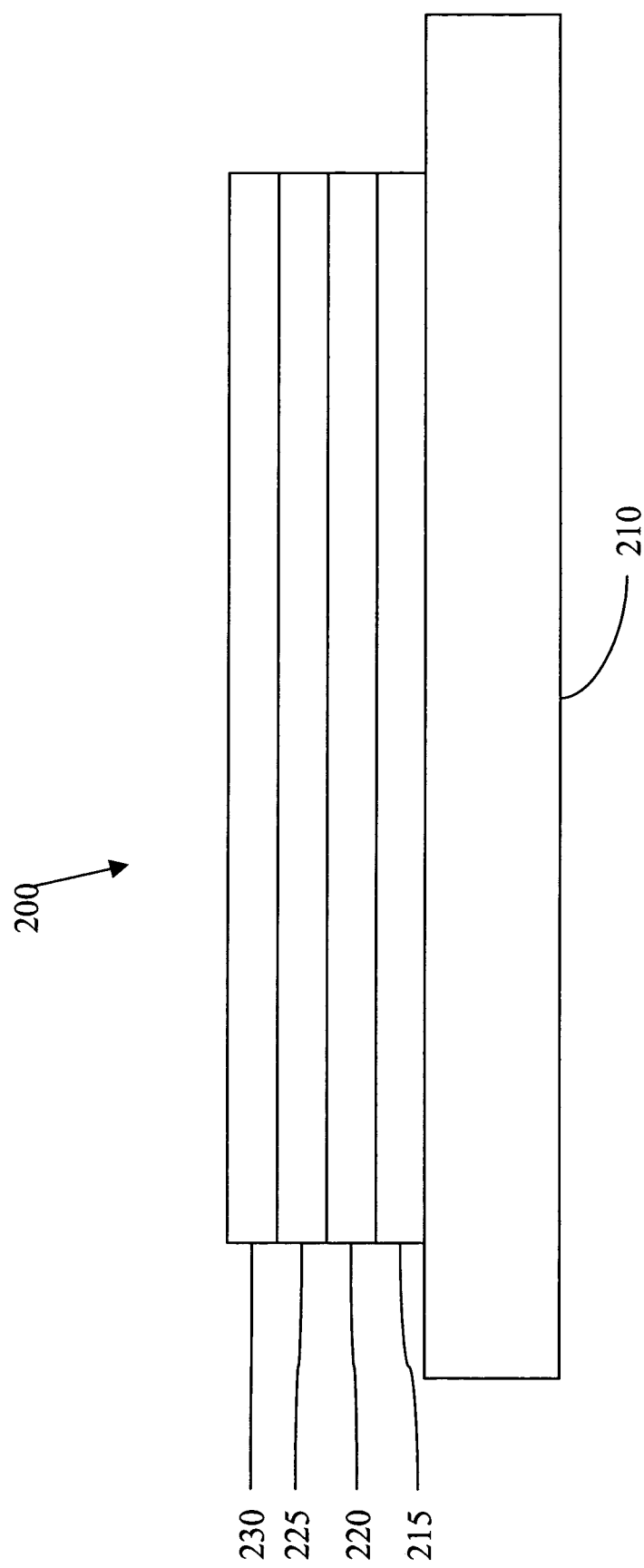
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers.

The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In an embodiment of the present invention, a phosphorescent compound having improved efficiency when incorporated into an OLED is provided. The emissive compound has the following structure (Formula I):

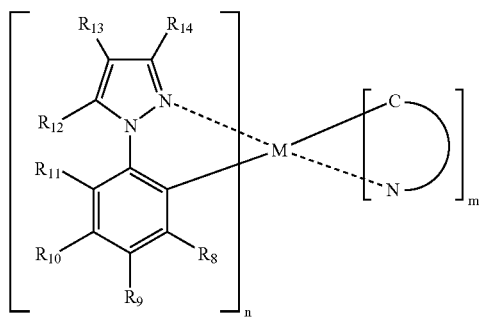

wherein

M is a metal having an atomic weight greater than 40;

(C—N) is a substituted or unsubstituted cyclometallated ligand, and (C—N) is different from at least one other ligand attached to the metal;

each of $R_8$ through $R_{14}$ is independently selected from hydrogen, alkyl, alkenyl, alkynyl, alkylaryl, CN, $CF_3$, $CO_2R$, C(O)R, $NR_2$, $NO_2$, OR, halo, aryl, heteroaryl, substituted aryl, substituted heteroaryl, or a heterocyclic group, wherein each R is independently selected from the group consisting of H, alkyl, alkaryl, and aryl;

additionally or alternatively, any two adjacent substituted positions together form, independently, a fused 4- to 7-member cyclic group, wherein said cyclic group is cycloalkyl, cycloheteroalkyl, aryl, or heteroaryl, and wherein the 4- to 7-member cyclic group may be optionally substituted with substituent R;

m has a value of at least 1;

n has a value of at least 1; and m+n is the maximum number of ligands that may be attached to the metal.

M may be any metal having an atomic weight greater than 40. Preferred metals include Ir, Pt, Pd, Rh, Re, Os, Tl, Pb, Bi, In, Sn, Sb, Te, Au, and Ag. More preferably, the metal is Ir or Pt. Most preferably, the metal is Ir.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, $CO_2R$, C(O)R, $NR_2$, cyclic-amino, $NO_2$, and OR, wherein each R is independently selected from the group consisting of H, alkyl, alkaryl, and aryl.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, $CO_2R$, C(O)R, $NR_2$, cyclic-amino, $NO_2$, and OR, wherein each R is independently selected from the group consisting of H, alkyl, alkaryl, and aryl.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, C(O)R, $NR_2$, cyclic-amino, $NO_2$, and OR, wherein each R is independently selected from the group consisting of H, alkyl, alkaryl, and aryl.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, $CO_2R$, C(O)R, $NR_2$, cyclic-amino, $NO_2$, and OR, wherein each R is independently selected from the group consisting of H, alkyl, alkaryl, and aryl.

The terms "alkylaryl" as used herein contemplates an alkyl group that has as a substituent an aromatic group. Additionally, the alkylaryl group may be optionally substituted on the aryl with one or more substituents selected from halo, CN, $CO_2R$, C(O)R, $NR_2$, cyclic-amino, $NO_2$, and OR, wherein each R is independently selected from the group consisting of H, alkyl, alkaryl, and aryl.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like.

The term "aryl" or "aromatic group" as used herein contemplates single-ring groups and polycyclic ring systems. The polycyclic rings may have two or more rings in which two carbons are common by two adjoining rings (the rings are "fused") wherein at least one of the rings is aromatic, e.g., the other rings can be cycloalkyls, cycloalkenyls, aryl, heterocycles and/or heteroaryls.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls.

All value ranges, for example those given for n and m, are inclusive over the entire range. Thus, for example, a range between 0-4 would include the values 0, 1, 2, 3 and 4.

(C—N) represents a photoactive ligand, and this ligand is referred to as "photoactive" because it is believed that it directly contributes to the photoactive properties of the emissive material. Whether a ligand is photoactive depends upon the specific compound in which the ligand is present. For example, each of the ppy ligands of Ir(ppy)$_3$ is considered photoactive. However, in the compound (ppy)$_2$IrX, having two ppy ligands coordinated to the Ir, as well as an X ligand coordinated to the Ir, the ppy ligands may not be photoactive, particularly if the X ligand has a lower triplet energy than the ppy ligands. Preferred (C—N) ligands include tpy, ppy, 4,6-F$_2$ppy, 4-MeO-4,6-F$_2$ppy, 4'-DMA-4,6-F$_2$ppy, 2-ppy, and 2-thpy. Other examples of photoactive ligands are disclosed in U.S. patent application Ser. No. 10/289,915 to Brown et al, which is incorporated by reference in its entirety.

n represents the number of ligands of a particular type, which do not emit at room temperature. n has a value of at least 1. m represents the number of photoactive ligands of a particular type, and has a value of at least 1. The maximum number of ligands that maybe attached to the metal is m+n.

In a preferred embodiment, n is 2. More preferably, each ligand is organometallic.

The compound of the embodiments of the present invention comprises at least one photoactive ligand of Formula I and a heavy metal ion such that the resulting material has (i) a carbon-metal bond and (ii) a nitrogen-metal bond. Thus the compounds of the embodiments of the present invention comprise a partial structure of

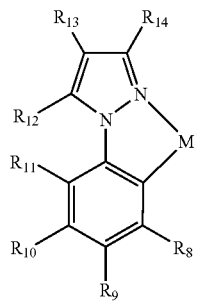

wherein the metal M and each substituent R are defined according to the definition of Formula I.

In an embodiment of the invention, the emissive compound comprises a ligand having the structure:

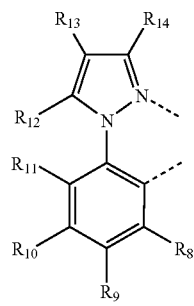

wherein each R is defined according to the definition of Formula I.

An embodiment of the invention comprises a compound with the structure

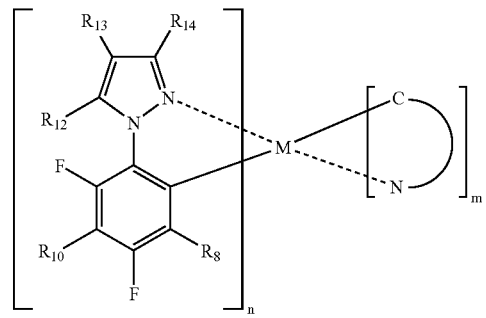

wherein the metal M, each substituent R, m, n, and (C—N) are defined according to the definition of Formula I. Preferably, M is iridium. In another preferred embodiment, R$_8$, R$_{10}$, and R$_{12}$-R$_{14}$ are hydrogen. In a most preferred embodiment, n is 2 and m is one. An embodiment of this invention includes a ligand with the following structure:

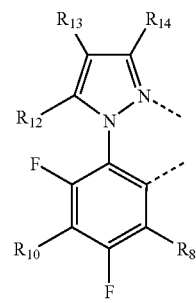

Preferably, each R is hydrogen.

Preferred embodiments of the invention include the following structures:

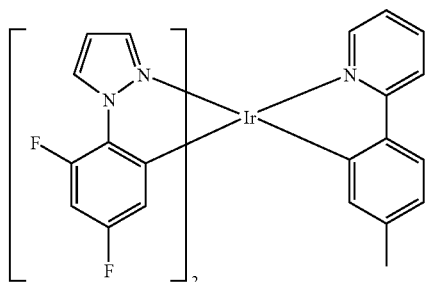

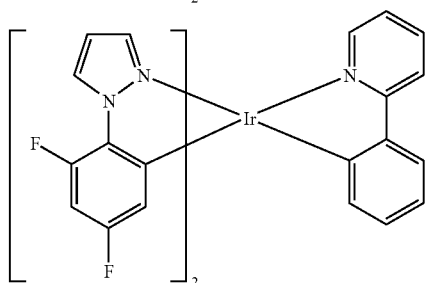

-continued

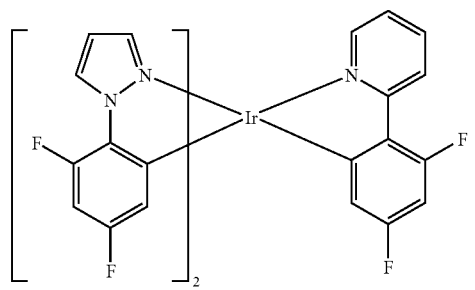

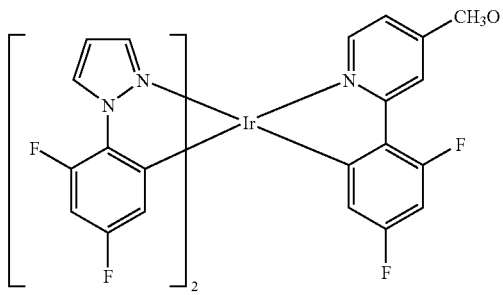

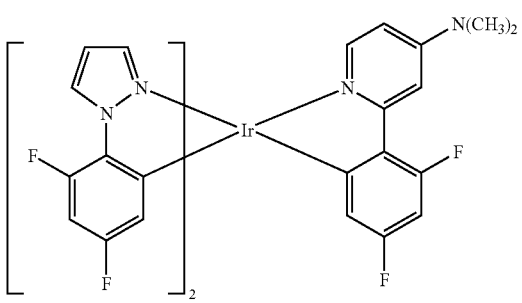

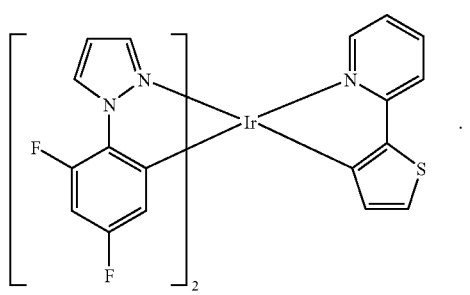

In another embodiment, the compound of Formula I comprises a structure such that n is the maximum number of ligands that may be attached to the metal M, and m is zero. In this embodiment, M and each each of substituents $R_8$ through $R_{14}$ is defined according to the definition of Formula I, with the notable exception that none $R_8$ through $R_{14}$ is a cyano group. An embodiment of this invention includes a compound with the structure

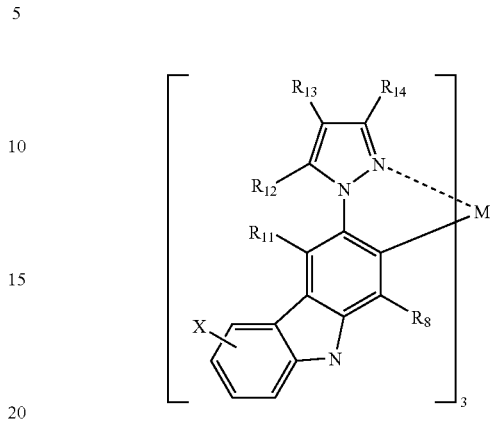

wherein X is independently selected from hydrogen, alkyl, alkenyl, alkynyl, alkylaryl, CN, $CF_3$, $CO_2R$, C(O)R, $NR_2$, $NO_2$, OR, halo, aryl, heteroaryl, substituted aryl, substituted heteroaryl, or a heterocyclic group, wherein each R is independently selected from the group consisting of H, alkyl, alkaryl, and aryl. Preferably, M is iridium and each of $R_8$ through $R_{14}$ is hydrogen. An embodiment of this invention includes a ligand with the following structure:

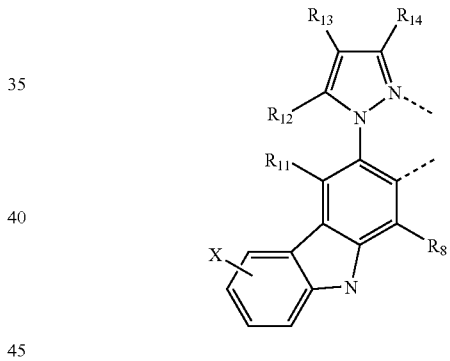

Preferably, each of $R_8$ through $R_{14}$ is hydrogen.

Homoleptic (all the ligands attached to the metal center have the same structure) iridium complexes employing phenylpyrazole derivatives as ligands, such as the above embodiment, have been found to be display poor electroluminescent qualities. Such complexes are observed not to emit light at room temperature, in either fluid solution or in the solid state. But a cyano substituted iridium phenylpyrazole complex has previously been reported to emit light at room temperature at a peak wavelength of around 450 nm. Kwon et al., "Blue Phosphorescent Cyclometalated Iridium Complex through phenylpyrazole derivatives: Synthesis, Characterization and B3LYP Density functional Theory (DFT) Calculations," 4th International Conference on Electroluminescence of Molecular Materials and Related Phenomena, Aug. 27-30, 2004, Jeju Island, Korea. Homoleptic iridium complexes are observed to emit in the UV region at 77K at peak wavelength values around 400 nm. It is believed that employing certain substituents on the phenylpyrazole ligand significantly improves luminescent efficiencies. Specifically it is believed that substitution of phenyl, napthyl, or pyridyl groups in the phenylpyrazole ligand improves the device lifetime and enhances electroluminescent efficiencies. Additionally, it is believed that fusing the adjacent substituents of the phenylpyrazole ligand also improves the lifetime and efficiency of the device. These substituents are provided as non-limiting examples, and other substituted phenylpyrazole ligands exhibiting improved lifetime and enhanced luminescence may be employed.

In a preferred embodiment, one or more of the substituents $R_8$ through $R_{14}$, as defined in Formula I, is phenyl, napthyl, or pyridyl, which may be substituted or unsubstituted. Preferably at least one substituent $R_8$ through $R_{14}$ is phenyl. Preferred embodiments include compounds having the following structures:

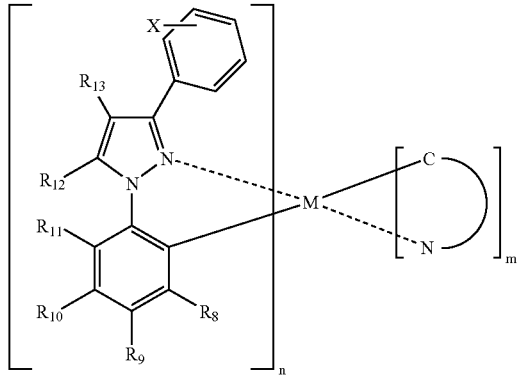

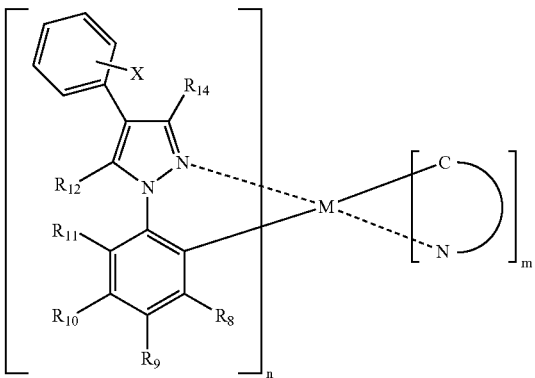

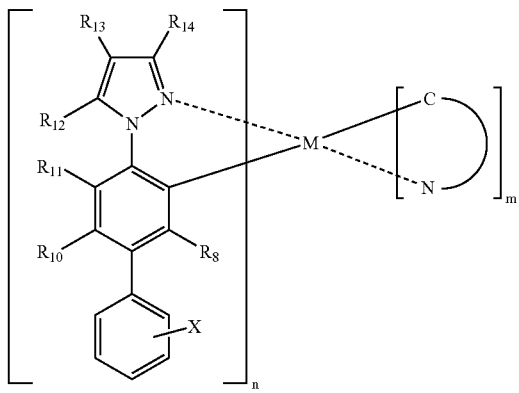

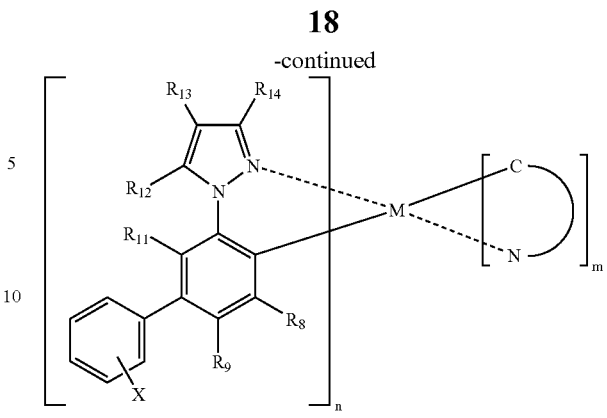

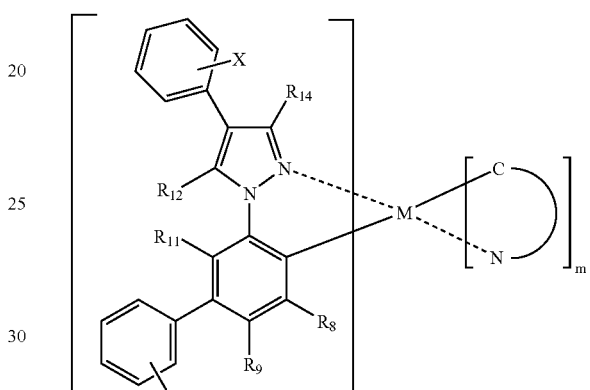

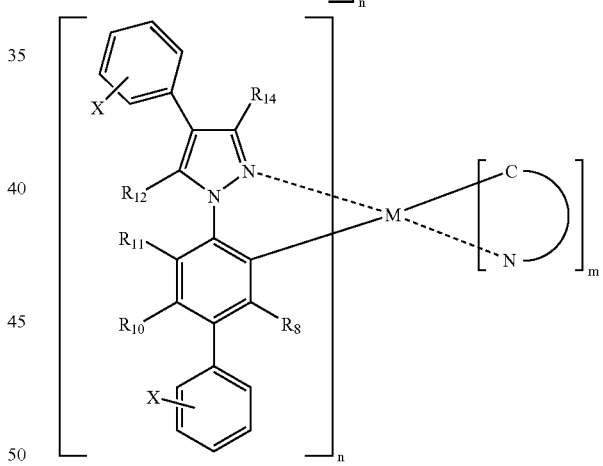

wherein the metal M, each of substituents $R_8$ through $R_{14}$, m, n, and (C—N) is defined according to the definition of Formula I. X is independently selected from hydrogen, alkyl, alkenyl, alkynyl, alkylaryl, CN, $CF_3$, $CO_2R$, C(O)R, $NR_2$, $NO_2$, OR, halo, aryl, heteroaryl, substituted aryl, substituted heteroaryl, or a heterocyclic group, wherein each R is independently selected from the group consisting of H, alkyl, alkaryl, and aryl. Additionally or alternatively, any two adjacent substituted positions together form, independently, a fused 4- to 7-member cyclic group, which may be cycloalkyl, cycloheteroalkyl, aryl, or heteroaryl, and the 4- to 7-member cyclic group may be further substituted by substituent X. Preferred embodiments of this invention include ligands with the following structure:

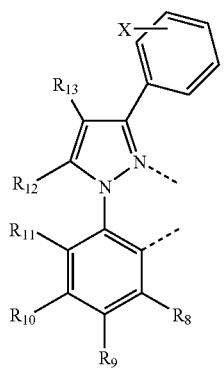

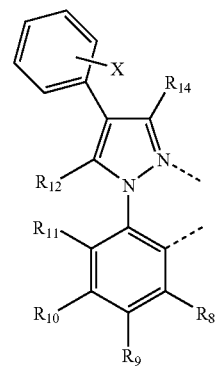

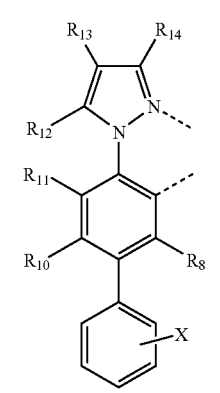

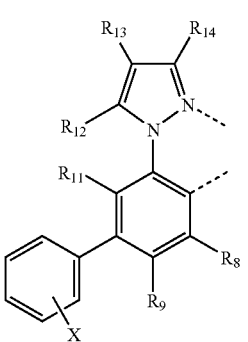

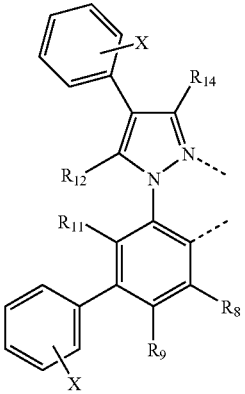

-continued

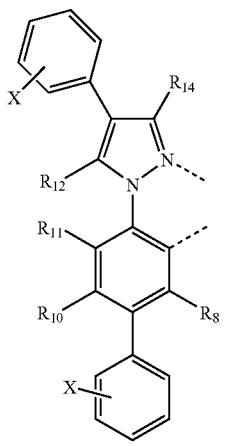

wherein each substituent $R_8$ through $R_{14}$ is defined according to the definition of Formula I. X is independently selected from hydrogen, alkyl, alkenyl, alkynyl, alkylaryl, CN, $CF_3$, $CO_2R$, C(O)R, $NR_2$, $NO_2$, OR, halo, aryl, heteroaryl, substituted aryl, substituted heteroaryl, or a heterocyclic group, wherein each R is independently selected from the group consisting of H, alkyl, alkaryl, and aryl. Additionally or alternatively, any two adjacent substituted positions together form, independently, a fused 4- to 7-member cyclic group, which may be cycloalkyl, cycloheteroalkyl, aryl, or heteroaryl, and the 4- to 7-member cyclic group may be further substituted by substituent X.

In another embodiment, at least two substituents $R_8$ through $R_{14}$, as defined in Formula I, are fused to form a 4- to 7-member cyclic group, which may be optionally substituted. In preferred embodiments, the substituents form a 5- or 6-member cyclic groups. Preferred embodiments include compounds having the following structures:

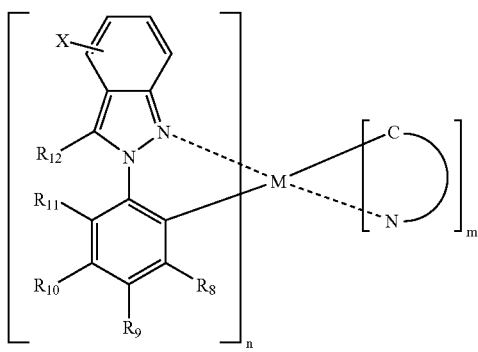
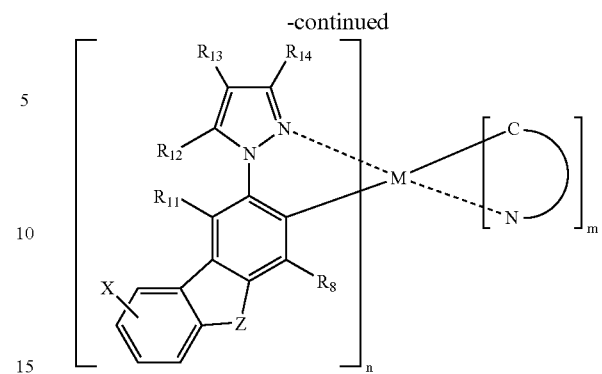
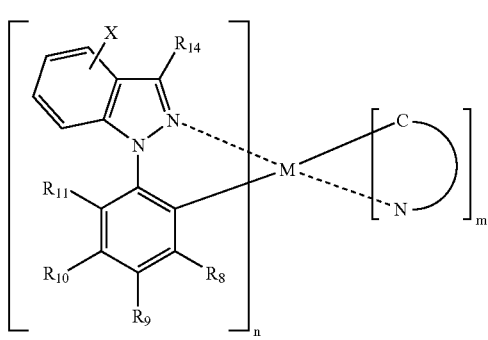
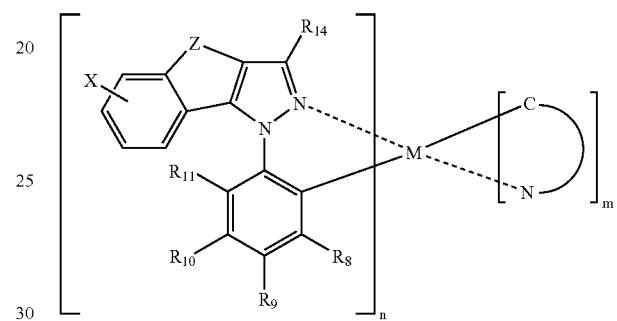
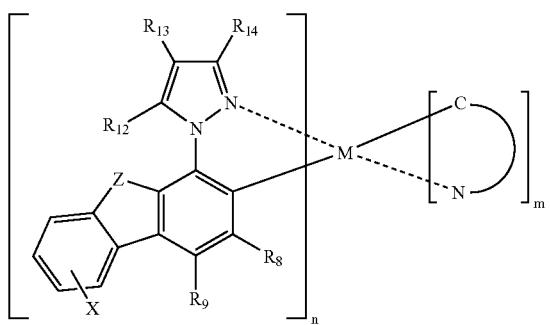
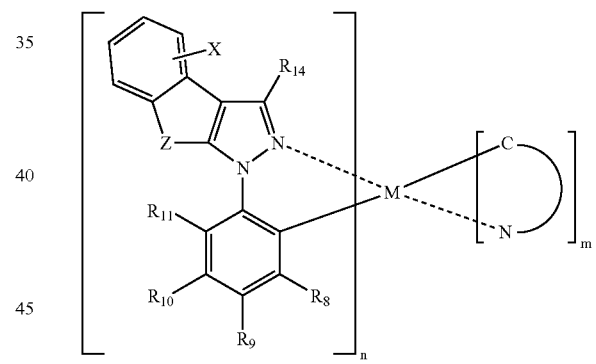
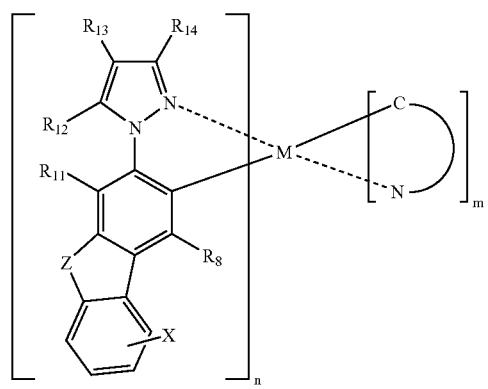
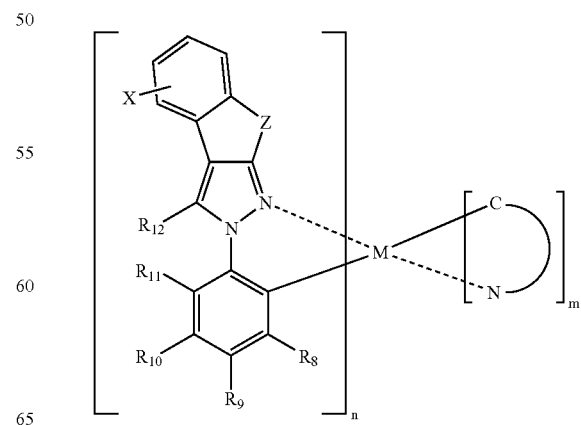

-continued

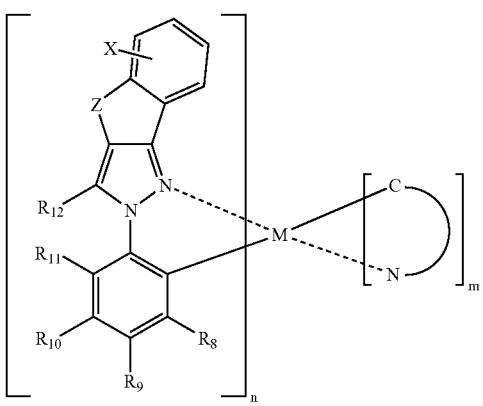

wherein the metal M, each of substituents $R_8$ through $R_{14}$, m, n, and (C—N) is defined according to the definition of Formula I. X is independently selected from hydrogen, alkyl, alkenyl, alkynyl, alkylaryl, CN, $CF_3$, $CO_2R$, C(O)R, $NR_2$, $NO_2$, OR, halo, aryl, heteroaryl, substituted aryl, substituted heteroaryl, or a heterocyclic group, wherein each R is independently selected from the group consisting of H, alkyl, alkaryl, and aryl. Additionally or alternatively, any two adjacent substituted positions together form, independently, a fused 4- to 7-member cyclic group, which may be cycloalkyl, cycloheteroalkyl, aryl, or heteroaryl, and the 4- to 7-member cyclic group may be further substituted by substituent X. Z is selected from —$CH_2$, —CRR, —NH, —NR, —O, —S, —SiR. Preferred embodiments of this invention include ligands with the following structure:

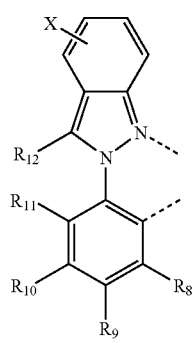

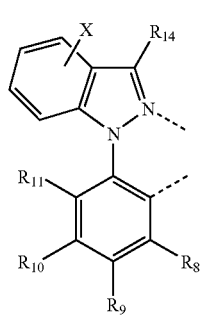

-continued

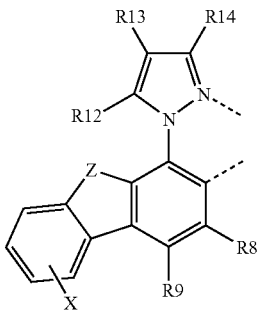

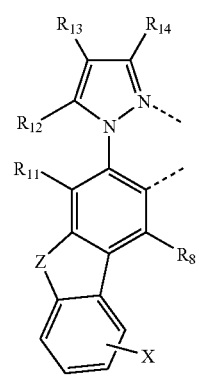

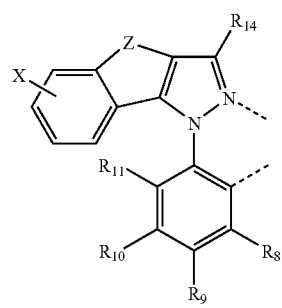

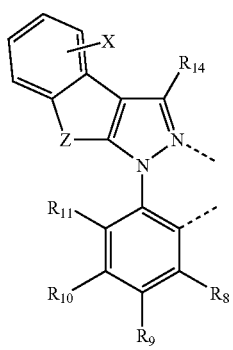

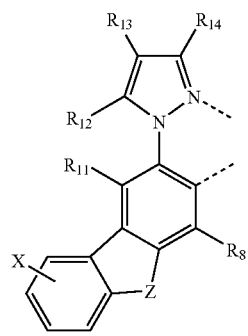

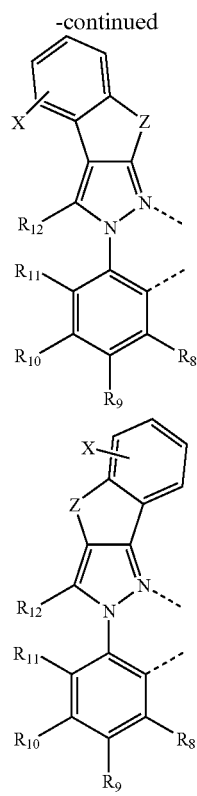

wherein each substituent $R_8$ through $R_{14}$ is defined according to the definition of Formula I. X is independently selected from hydrogen, alkyl, alkenyl, alkynyl, alkylaryl, CN, $CF_3$, $CO_2R$, $C(O)R$, $NR_2$, $NO_2$, OR, halo, aryl, heteroaryl, substituted aryl, substituted heteroaryl, or a heterocyclic group, wherein each R is independently selected from the group consisting of H, alkyl, alkaryl, and aryl. Additionally or alternatively, any two adjacent substituted positions together form, independently, a fused 4- to 7-member cyclic group, which may be cycloalkyl, cycloheteroalkyl, aryl, or heteroaryl, and the 4- to 7-member cyclic group may be further substituted by substituent X. Z is selected from —$CH_2$, —CRR, —NH, —NR, —O, —S, —SiR.

In a preferred embodiment of the present invention, the substituted phenylpyrazole metal complex is heteroleptic. In a heteroleptic metal complex, a ligand attached to the metal center has a different structure from at least one other ligand. Preferably, at least one ligand is a phosphorescent emissive ligand at room temperature and at least one ligand is not a phosphorescent emissive ligand at room temperature. More preferably, only one ligand is a phosphorescent emitter at room temperature. A heteroleptic complex of embodiments of the present invention has several advantages over a homoleptic metal complex. It is believed that the likelihood of intermolecular quenching is lower for heteroleptic complexes of embodiments of the present invention than for homoleptic complexes due to lower density of favorable energy transfer sites associated with heteroleptic complexes. For example, bis-(1-(4,6-difluoro-phenyl)pyrazolato,N, $C^{2'}$) iridium (phenylpyridinato,N, $C^2$), which is a specific embodiment of the present invention in which there is only one emissive ligand attached to the metal center, the triplet is localized on the emissive ligand (i.e. phenylpyridinato). A favorable reduction of intermolecular quenching leads to increased device efficiency.

Moreover, it is believed that substituting fluorine in ligands of the embodiments of the present invention generally increases the triplet energy of the substituted ligands. Consequently, one method of designing for a ligand with sufficiently high triplet energy such that the ligand is non-emissive is by substituting fluorine for hydrogens of the phenylpyrazole ligands of the embodiments of the present invention.

In a preferred embodiment, in which the cyclometallated complex is heteroleptic, an emissive ligand has a triplet energy corresponding to a wavelength that is at least 80 nm greater than the wavelength corresponding to the triplet energy of non-emissive ligands. The emissive ligand may have a triplet energy corresponding to a wavelength of 500-520 nm. In another embodiment, the emissive ligand has a triplet energy corresponding to a wavelength greater than 590 nm. In a preferred embodiment, the emissive ligand has a triplet energy corresponding to a wavelength less than 480 nm. In one embodiment, there is only one emissive ligand at room temperature. Ligands that are emissive in certain compounds may be non-emissive in other compounds due to the presence of other ligands having lower triplet energy bound to the same metal. In this case, energy is transferred from the ligand with higher triplet energy to the ligand with lower triplet energy, and consequently, the ligand initially with the higher triplet energy does not contribute to the emission. In another embodiment, there is only one emissive ligand at room temperature and this ligand is organometallic.

In another embodiment, each ligand coordinated to the metal forms an organometallic bond with the metal. Organometallic ligands are believed to be more thermally stable than non-organometallic ligands, when coordinated to third row transition metals, such as Ir and Pt. In a preferred embodiment, in which the cyclometallated complex is heteroleptic, two non-emissive ligands are coordinated to iridium. In this case, the luminescent spectrum is observed to be blue-shifted relative to the spectrum of a homoleptic organometallic cyclometallated complex of embodiments of the present invention. The blue spectral shift is believed to result from a strong field interaction between the carbon and metal atoms in an organometallic complex.

For the synthesized complexes of the present invention, it was observed that the meridional and facial isomers behave similarly. Thus, it is believed that the choice of positional isomers does not significantly affect device performance. Meridional isomers may be preferred as they are found to be synthesized more readily. For example, a facial isomer is generally synthesized by converting a meridional isomer. Facial isomers may be preferred, as they are presently the most common isomers in organometallic compounds.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

Material Definitions:

As used herein, abbreviations refer to materials as follows:

CBP: 4,4'-N,N-dicarbazole-biphenyl
m-MTDATA 4,4',4''-tris(3-methylphenylphenlyamino)triphenylamine
$Alq_3$: 8-tris-hydroxyquinoline aluminum
Bphen: 4,7-diphenyl-1,10-phenanthroline
n-BPhen: n-doped BPhen (doped with lithium)
$F_4$-TCNQ: tetrafluoro-tetracyano-quinodimethane
p-MTDATA: p-doped m-MTDATA (doped with $F_4$-TCNQ)
$Ir(ppy)_3$: tris(2-phenylpyridine)-iridium
$Ir(ppz)_3$: tris(1-phenylpyrazoloto,N,C(2')iridium(III)
BCP: 2,9-dimethyl-4,7-diphenyl-1,10-phenanthroline
TAZ: 3-phenyl-4-(1'-naphthyl)-5-phenyl-1,2,4-triazole
CuPc: copper phthalocyanine.
ITO: indium tin oxide
NPD: N,N'-diphenyl-N-N'-di(1-naphthyl)-benzidine
TPD: N,N'-diphenyl-N-N'-di(3-toly)-benzidine
BAlq: aluminum(III)bis(2-methyl-8-hydroxyquinolinato)4-phenylphenolate
mCP: 1,3-N,N-dicarbazole-benzene
DCM: 4-(dicyanoethylene)-6-(4-dimethylaminostyryl-2-methyl)-4H-pyran
DMQA: N,N'-dimethylquinacridone
PEDOT:PSS: an aqueous dispersion of poly(3,4-ethylene-dioxythiophene) with polystyrenesulfonate (PSS)
tpy: 2-(p-tolyl)pyridine
ppy: 2-phenylpyridine
4,6-$F_2$ppy: 2-(4',6'-difluorophenyl)pyridine
4-MeO-4,6-$F_2$ppy: 2-(4',6'-difluorophenyl)-4-methoxypyridine
4'-DMA-4,6-$F_2$ppy: 2-(4',6'-difluorophenyl)-4-(N,N-dimethylamino)pyridine
2-thpy: 2-(2'-thienyl)pyridine
(46dfppz)$_2$Ir(ppy): bis(1-(4,6-difluorophenyl)pyrazolato-N, $C^{2'}$)Iridium(III) (2-phenylpyridinato-N,$C^{2'}$)
(46dfppz)$_2$Ir(tpy): bis(1-(4,6-difluorophenyl)pyrazolato-N, $C^{2'}$)Iridium(III) (2-(p-tolyl)pyridinato-N,$C^{2'}$)
(46dfppz)$_2$Ir(4',6'-$F_2$ppy): bis(1-(4,6-difluorophenyl)pyrazolato-N,$C^{2'}$)Iridium(III) (2-(4',6'-difluorophenyl)pyridinato-N,$C^{2'}$)
(46dfPpz)$_2$Ir(4-MeO-4',6'-$F_2$ppy): bis(1-(4,6-difluorophenyl)pyrazolato-N,$C^{2'}$)Iridium(III) (2-(4',6'-difluorophenyl)-4-methoxypyridinato-N,$C^{2'}$)
(46dfPpz)$_2$Ir(4-DMA-4',6'-$F_2$ppy): bis(1-(4,6-difluorophenyl)pyrazolato-N,$C^{2'}$)Iridium(III) (2-(4',6'-difluorophenyl)-4-(N,N'-dimethylamino)pyridinat o-N,$C^{2'}$)
3bppz: 1-(3-biphenyl)pyrazole
4bppz: 1-(4-biphenyl)pyrazole
14dppz: 1,4-diphenylpyrazole
4bpppz: 1-(4-biphenyl)-4-phenylpyrazole
2dmflpz: 1-(2-(9,9-dimethyl)fluorenyl)pyrazole
3dmflpz: 1-(3-(9,9-dimethyl)fluorenyl)pyrazole
fac-Ir(3bppz)$_3$: fac-tris(1-(3-biphenyl)pyrazolato-N,$C^{2'}$)iridium(III)
fac-Ir(4bppz)$_3$: fac-tris(1-(4-biphenyl)pyrazolato-N,$C^{2'}$)iridium(III)
fac-Ir(14dppz)$_3$: fac-tris(1,4-diphenylpyrazolato-N,$C^{2'}$)iridium(III)
fac-Ir(4bpppz)$_3$: fac-tris(1-(4-biphenyl)-4-phenylpyrazolato-N,$C^{2'}$)iridium(III)
fac-Ir(2dmflpz)$_3$: fac-tris(1-(2-(9,9dimethyl)fluorenyl)pyrazolato-N,$C^{2'}$)iridium(III)

EXPERIMENTAL

Specific representative embodiments of the invention will now be described, including how such embodiments may be made. It is understood that the specific methods, materials, conditions, process parameters, apparatus and the like do not necessarily limit the scope of the invention.

Example 1

General synthetic scheme for a substituted phenylpyrazole

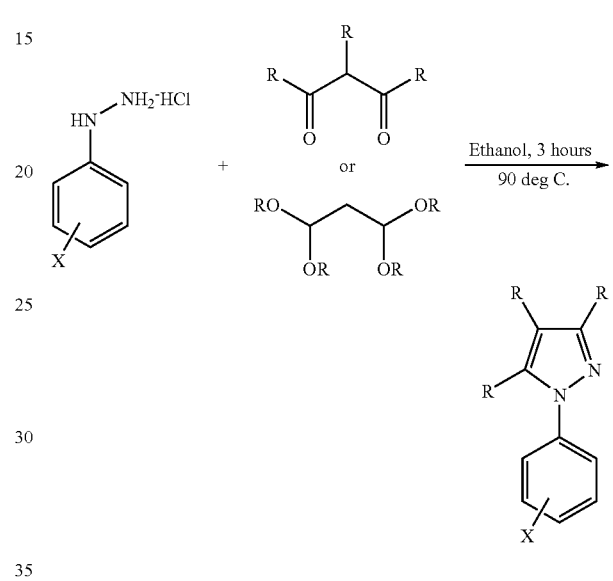

Ligands synthesized through the above synthetic route are summarized in Table I.

TABLE I

| Compound | Phenylpyrazole ligand |
|---|---|
| (46dfppz)$_2$Ir(ppy)<br>(46dfppz)$_2$Ir(tpy)<br>(46dfppz)$_2$Ir(4',6'-$F_2$ppy)<br>(46dfppz)$_2$Ir(4-MeO-4',6'-$F_2$ppy)<br>(46dfppz)$_2$Ir(4'-DMA-4,6-$F_2$ppy) | |
| fac-Ir(14dppz)$_3$ | |

Example 2

General synthetic scheme for a biphenylpyrazole

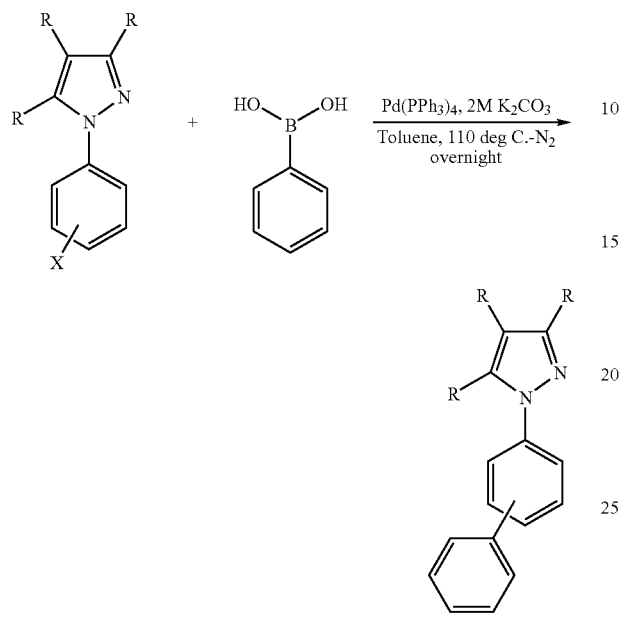

Ligands synthesized through the above synthetic route are summarized in Table II.

TABLE II

| Compound | Phenylpyrazole ligand |
|---|---|
| fac-Ir(3bppz)$_3$ | |
| fac-Ir(4bppz)$_3$ | |
| fac-Ir(4bpppz)$_3$ | |

Example 3

Synthesis of 2dmflpz ligand

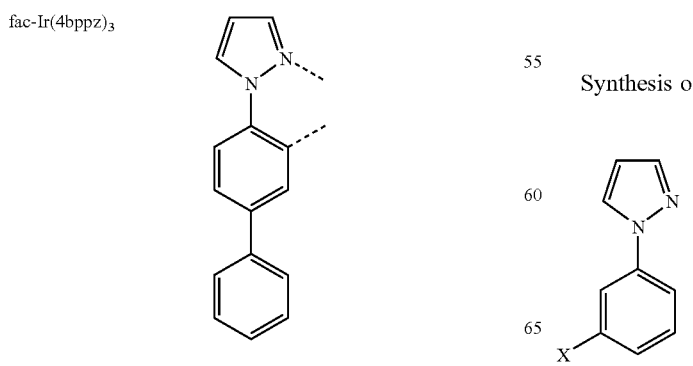

1. $I_2$—$H_5IO_6$, 80% aq. HOAc
   80 deg C. uner $N_2$ -4 hrs.
2. $CH_3I$, $BzEt_3NCl$, 50% aq. NaOH
   RT in DMSO under $N_2$ - 18 hrs.
3. Pyrazole, CuI, $K_2CO_3$
   dodecane, 1,2-trans-CDA
   110 deg C. indioxane udner N2 -24 hrs.

Example 4

Synthesis of 3dmflpz ligand

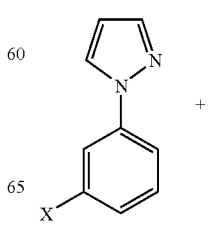
+

-continued

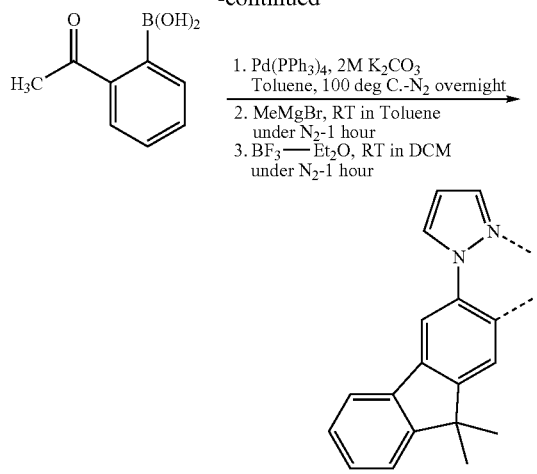

Example 5

Synthesis of Meridional Isomers of (46dfppz)₂Ir(ppy), (46dfppz)₂Ir(tpy), (46dfppz)₂Ir(4',6'-F₂ppy), (46dfppz)₂Ir(4-MeO-4',6'-F₂ppy), and (46dfppz)₂Ir(4'-DMA-4',6'-F₂ppy)

[(46dfppz)₂IrCl]₂ complex, 1-1.05 equivalent of the appropriate ligand, 5-10 equivalent of K₂CO₃ were heated to 140-145° C. under inert atmosphere in glycerol for 20-24 hours. After the mixture was cooled to room temperature, distilled water was added, and the resulting precipitate was filtered off, washed with several portions of distilled water, and air-dried. The crude product was then flashed chromatographed on a silica column using dichloromethane to provide 60-80% of pure meridional heteroleptic iridium tris-cyclometalated complex.

Example 6

Synthesis of Facial Isomers of (46dfppz)₂Ir(ppy), (46dfppz)₂Ir(tpy), (46dfppz)₂Ir(4',6'-F₂ppy), (46dfppz)₂Ir(4-MeO-4',6'-F₂ppy), and (46dfppz)₂Ir(4-DMA-4',6'-F₂ppy)

An argon-degassed solution of the meridional complex in acetonitrile was irradiated with UV light (254 nm or 360 nm) for 24-48 hours, after which the solvent was removed in vacuo. The crude product was then chromatographed on a silica column using dichloromethane to provide >90% of pure facial heteroleptic iridium tris-cyclometalated complex.

Example 7

Synthesis of fac-Ir(3bppz)₃, fac-Ir(4bppz)₃, fac-Ir(14dppz)₃, fac-Ir(4bpppz)₃, fac-Ir(2dmflpz)₃, and Ir(ppz)₃

[(C^N)₂Ir(O^O)] complex, 1-1.1 equivalent of the appropriate cyclometalating ligand, were refluxed under inert gas atmosphere in glycerol for 20-24 hours. After the mixture was cooled to room temperature, distilled water was added, and the resulting precipitate was filtered off, washed with several portions of distilled water, and air-dried. The crude product was then flashed chromatographed on a silica column using dichloromethane to provide 60-80% of pure facial heteroleptic iridium tris-cyclometalated complex.

Table III summarizes the photophysical properties of compounds of Examples 5 and 6.

TABLE III

| Compound | Structure | CIE coordinates (PL in solution) | Room Temp. Emission (nm) | 77K Emission (nm) |
|---|---|---|---|---|
| (46dfppz)₂Ir(ppy) | | 0.14, 0.43 | 476 | 466, 502 |
| (46dfppz)₂Ir(tpy) | | 0.15, 0.41 | 476 | 466, 502 |

TABLE III-continued

| Compound | Structure | CIE coordinates (PL in solution) | Room Temp. Emission (nm) | 77K Emission (nm) |
|---|---|---|---|---|
| (46dfppz)₂Ir(4',6'-F₂ppy) | | 0.14, 0.27 | 462, 488 | 448, 480 |
| (46dfppz)₂Ir(4-MeO-4',6'-F₂ppy) | | 0.14, 0.19 | 454, 478 | 460, 440, 432 |
| (46dfppz)₂Ir(4'-DMA-4',6'-F₂ppy). | | 0.15, 0.13 | 446, 466 | 430, 456 |

Table IV summarizes the electrochemical and photophysical properties of the fac-Ir(C—N)₃ complexes. The oxidation and reduction potentials were measured in anhydrous DMF using ferrocene as reference. All reduction potentials are irreversible. The spectral and lifetime data were obtained using 2-Me THF solutions that were bubble degassed with N₂.

TABLE IV

| Complex | $E_{oxidation}$ | $E_{reduction}$ | Room Temp. $\lambda_{max}$ (nm) | Room Temp. Lifetime (μs) | 77 K $\lambda_{max}$ (nm) | 77 K Lifetime (μs) |
|---|---|---|---|---|---|---|
| Comparative Irppz | 0.390 | — | — | — | 414 | 14 |
| fac-Ir(3bppz)₃ | 0.427 | −2.916 | 466 | — | 460 | 26.9 |
| fac-Ir(4bppz)₃ | 0.644 | −3.048 | 420 | — | 414 | 20.8 |
| fac-Ir(14dppz)₃ | 0.393 | −3.060 | 426 | — | 422 | 5.7; 13.6 |
| fac-Ir(4bpppz)₃ | 0.424 | −2.879 | 478 | 2.6 | 472 | 32.6 |
| fac-Ir(2dmflpz)₃ | 0.321 | −3.049 | 478 | 1.7 | 476 | 28.8 |

Figure 3:
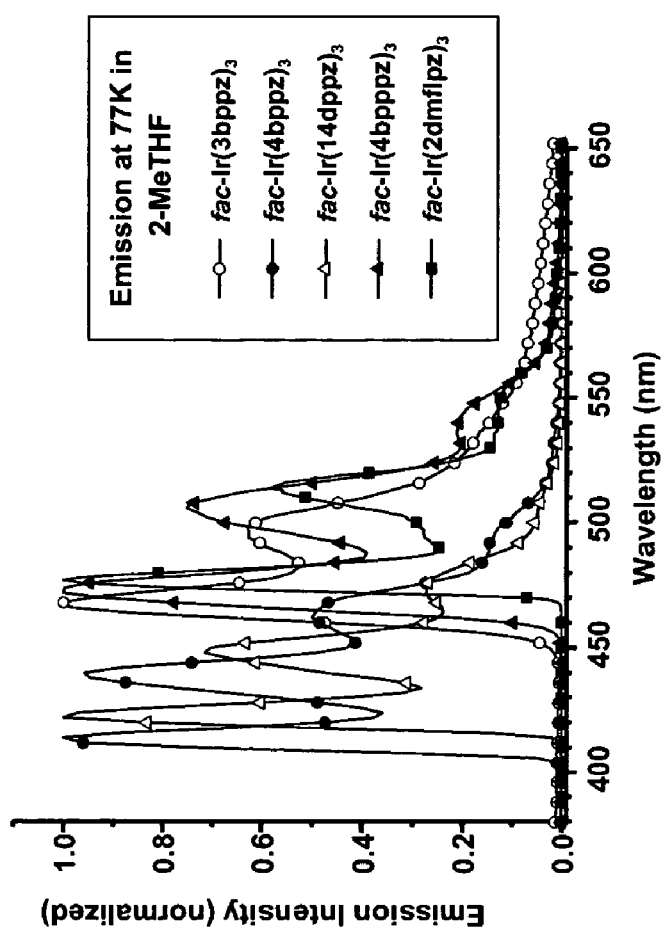
FIG. 3 shows the emission spectra at 77 K for fac-Ir(3bppz)$_3$, fac-Ir(4bppz)$_3$, fac-Ir(14dppz)$_3$, fac-Ir(4bpppz)$_3$, fac-Ir(2dmflpz)$_3$.

FIG. 3 shows the emission spectra at 77 K for fac-Ir(3bppz)₃, fac-Ir(4bppz)₃, fac-Ir(14dppz)₃, fac-Ir(4bpppz)₃, fac-Ir(2dmflpz)₃.

Figure 4:
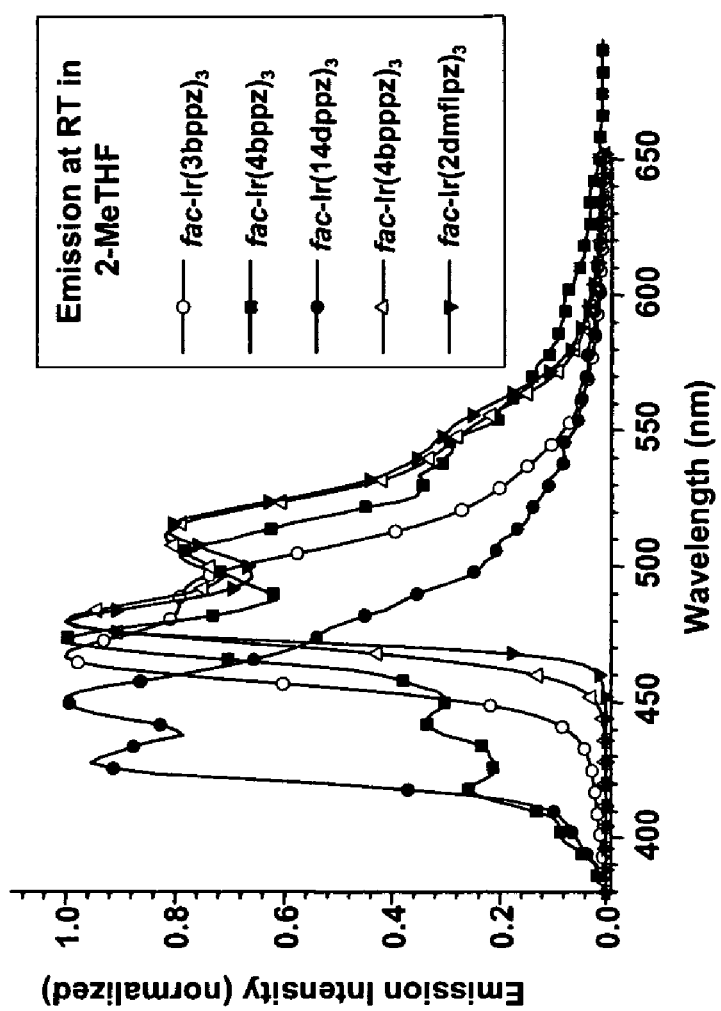
FIG. 4 shows the emission spectra at room temperature for fac-Ir(3bppz)$_3$, fac-Ir(4bppz)$_3$, fac-Ir(14dppz)$_3$, fac-Ir(4bpppz)$_3$, fac-Ir(2dmflpz)$_3$.

FIG. 4 shows the emission spectra at room temperature for fac-Ir(3bppz)₃, fac-Ir(4bppz)₃, fac-Ir(14dppz)₃, fac-Ir(4bpppz)₃, fac-Ir(2dmflpz)₃.

Figure 5:
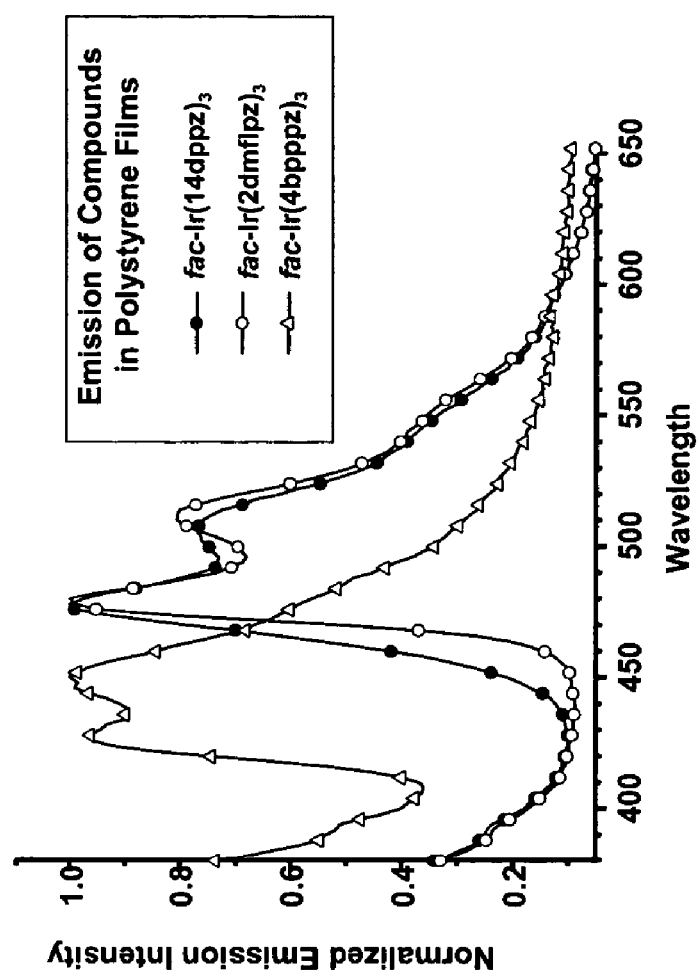
FIG. 5 shows the emission spectra for fac-Ir(14dppz)$_3$, fac-Ir(4bpppz)$_3$, fac-Ir(2dmflpz)$_3$ in polystyrene at room temperature.

FIG. 5 shows the emission spectra for fac-Ir(14dppz)₃, fac-Ir(4bpppz)₃, fac-Ir(2dmflpz)₃ in polystyrene at room temperature.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

What is claimed is:

1. A compound, having the structure:

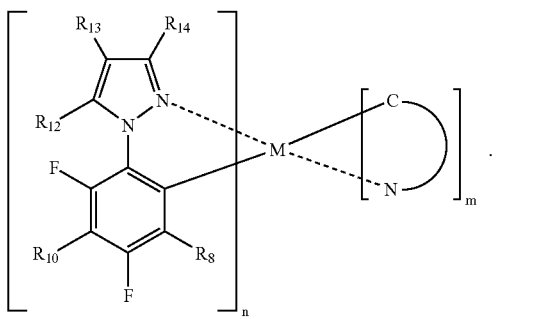

wherein
M is a metal having an atomic weight greater than 40;
(C—N) is a substituted or unsubstituted cyclometallated ligand, and (C—N) is different from at least one other ligand attached to the metal;
each $R_8$, $R_{10}$, and $R_{12}$ to $R_{14}$ is independently selected from hydrogen, alkyl, alkenyl, alkynyl, alkylaryl, CN, $CF_3$, $NO_2$, halo, aryl, heteroaryl, substituted aryl, substituted heteroaryl, or a heterocyclic group;
additionally or alternatively, any two adjacent substituted positions together form, independently, a fused 4- to 7-member cyclic group, wherein said cyclic group is cycloalkyl, cycloheteroalkyl, aryl, or heteroaryl, and wherein the 4- to 7-member cyclic group may be optionally substituted with a substituent independently selected from hydrogen, alkyl, alkenyl, alkynyl, alkylaryl, CN, $CF_3$, $NO_2$, halo, aryl, heteroaryl, substituted aryl, substituted heteroaryl, or a heterocyclic group;
m has a value of at least 1;
n has a value of at least 1; and
m+n is the maximum number of ligands that may be attached to the metal.

2. The compound of claim 1, wherein n is 2.

3. The compound of claim 2, wherein each ligand is organometallic.

4. The compound of clam 1, wherein M is selected from the group consisting of Ir, Pt, Pd, Rh, Re, Ru, Os, Tl, Pb, Bi, In, Sn, Sb, Te, Au, or Ag.

5. The compound of claim 4, wherein M is Ir.

6. The compound of claim 1, wherein at least one of $R_8$, $R_{10}$, $R_{12}$ to $R_{14}$, and a substituent of (C—N) is independently selected from substituted or unsubstituted phenyl, napthyl, or pyridyl.

7. The compound of claim 6, wherein at least one of $R_8$, $R_{10}$, $R_{12}$ to $R_{14}$, and a substituent of (C—N) is phenyl.

8. The compound of claim 7, wherein the compound has a structure selected from the group consisting of:

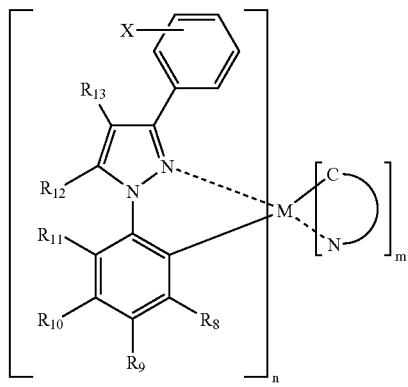

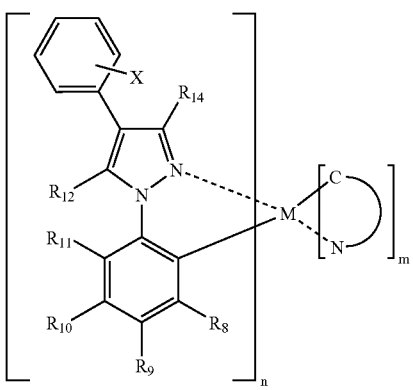

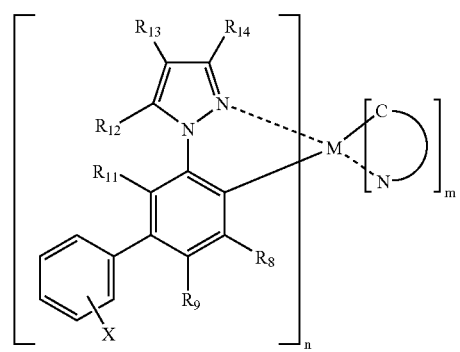

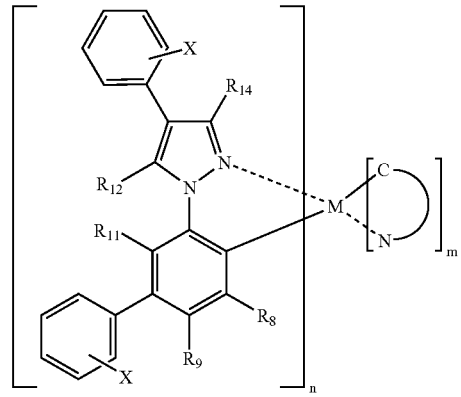

wherein X is independently selected from hydrogen, alkyl, alkenyl, alkynyl, alkylaryl, CN, CF$_3$, NO$_2$, halo, aryl, heteroaryl, substituted aryl, substituted heteroaryl, or a heterocyclic group;

additionally or alternatively, any two adjacent substituted positions together form, independently, a fused 4- to 7-member cyclic group, wherein said cyclic group is cycloalkyl, cycloheteroalkyl, aryl, or heteroaryl, and wherein the 4- to 7-member cyclic group may be further substituted by substituent X; and R$_9$ and R$_{11}$ are F.

9. The compound of claim 1, wherein the compound has a structure selected from the group consisting of:

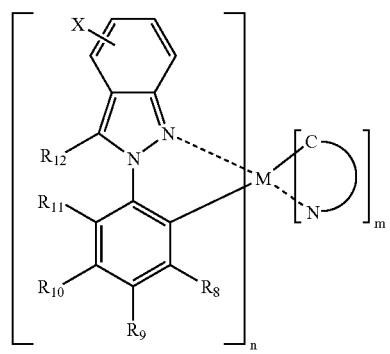

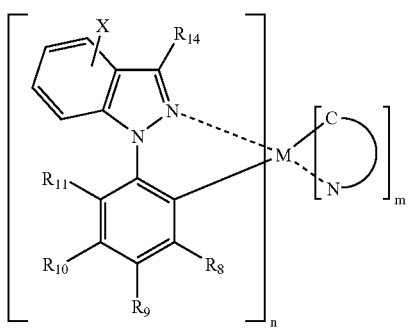

wherein X is independently selected from hydrogen, alkyl, alkenyl, alkynyl, alkylaryl, CN, CF$_3$, NO$_2$, halo, aryl, heteroaryl, substituted aryl, substituted heteroaryl, or a heterocyclic group;

additionally or alternatively, any two adjacent substituted positions together form, independently, a fused 4- to 7-member cyclic group, wherein said cyclic group is cycloalkyl, cycloheteroalkyl, aryl, or heteroaryl, and wherein the 4- to 7-member cyclic group may be further substituted by substituent X; and R$_9$ and R$_{11}$ are F.

10. The compound of claim 1, wherein the compound has a structure selected from the group consisting of:

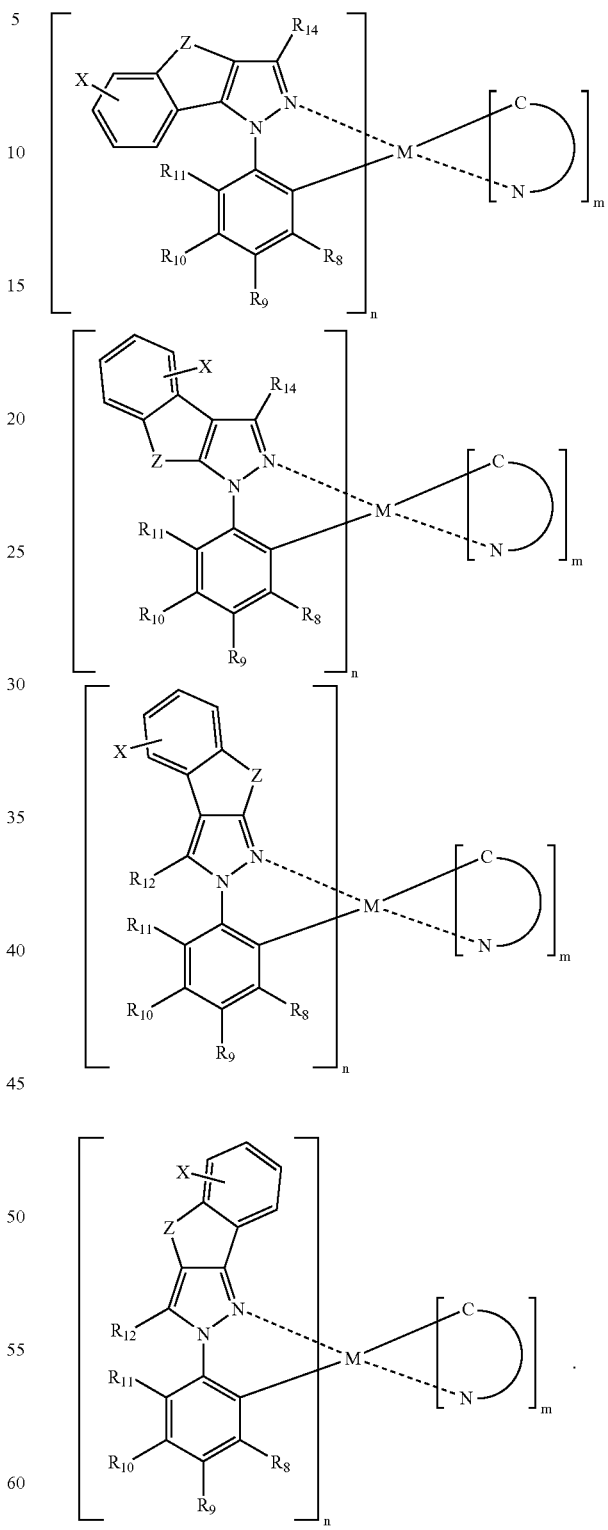

wherein X is independently selected from hydrogen, alkyl, alkenyl, alkynyl, alkylaryl, CN, CF$_3$, NO$_2$, halo, aryl, heteroaryl, substituted aryl, substituted heteroaryl, or a heterocyclic group;

additionally or alternatively, any two adjacent substituted positions together form, independently, a fused 4- to 7-member cyclic group, wherein said cyclic group is cycloalkyl, cycloheteroalkyl, aryl, or heteroaryl, and wherein the 4- to 7-member cyclic group may be further substituted by substituent X;

Z is selected from —CH$_2$, —CRR, —NH, —NR, —O, —S, —SiR wherein R is independently selected from hydrogen, alkyl, alkenyl, alkynyl, alkylaryl, CN, CF$_3$, NO$_2$, halo, aryl, heteroaryl, substituted aryl, substituted heteroaryl, or a heterocyclic group; and R$_9$ and R$_{11}$ are F.

11. The compound of claim 1, wherein the compound is a phosphorescent emissive material.

12. The compound of claim 1, wherein at least one ligand is a phosphorescent emissive ligand at room temperature and at least one ligand is not a phosphorescent emissive ligand at room temperature.

13. The compound of claim 12, wherein the ligand emissive in the compound at room temperature has a triplet energy corresponding to a wavelength that is at least 80 nm greater than the wavelength corresponding to the triplet energy of the ligand that is not emissive in the compound at room temperature.

14. The compound of claim 13, wherein the emissive ligand is organometallic.

15. The compound of claim 13, wherein the emissive ligand has a triplet energy corresponding to a wavelength of 500-520 nm.

16. The compound of claim 13, wherein the emissive ligand has a triplet energy corresponding to a wavelength greater than 590 nm.

17. The compound of claim 13, wherein each ligand is organometallic.

18. The compound of claim 17, wherein the emissive ligand has a triplet energy corresponding to a wavelength of 500-520 nm.

19. The compound of claim 17, wherein the emissive ligand has a triplet energy corresponding to a wavelength of 590 nm.

20. A compound, having the structure:

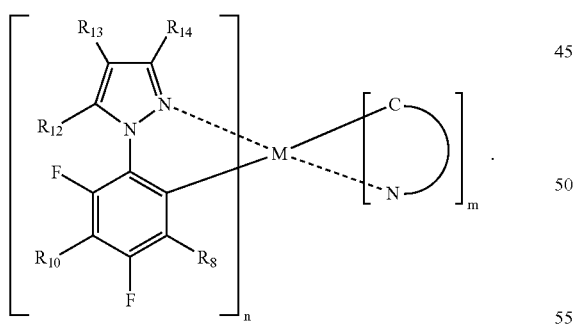

wherein
M is Ir;
(C—N) is a substituted or unsubstituted cyclometallated ligand, and (C—N) is different from at least one other ligand attached to the metal;
each R$_8$, R$_{10}$, and R$_{12}$ to R$_{14}$ are H;
m has a value of at least 1;
n has a value of at least 1; and
m+n is the maximum number of ligands that may be attached to the metal.

21. The compound of claim 20, wherein n is 2 and m is 1.

22. The compound of claim 21, having the structure:

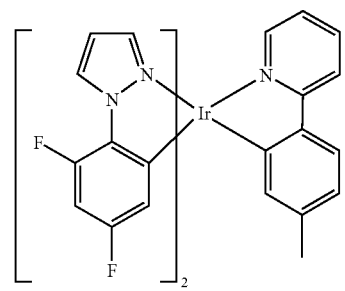

23. The compound of claim 21, having the structure:

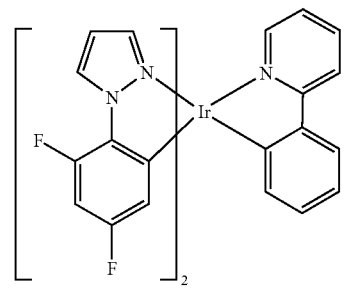

24. The compound of claim 21, having the structure:

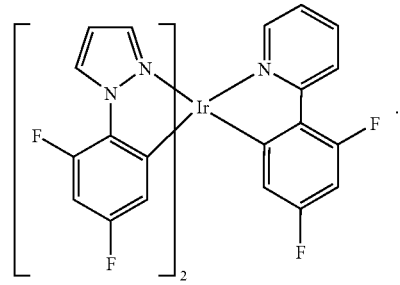

25. The compound of claim 21, having the structure:

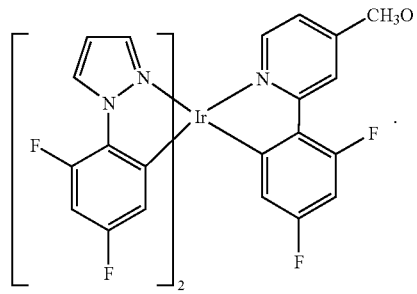

26. The compound of claim 21, having the structure:

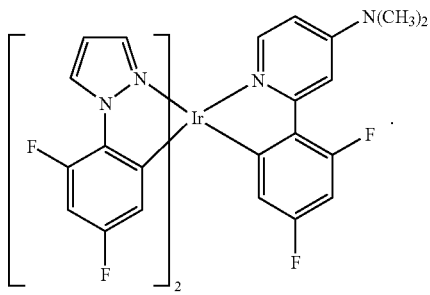

27. The compound of claim 21, having the structure:

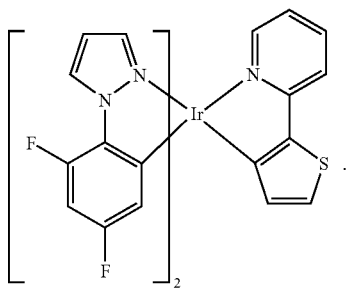

28. An organic light emitting device, comprising:
(a) an anode;
(b) a cathode; and
(c) an emissive layer disposed between and electrically connected to the anode and the cathode, the emissive layer further comprising a compound having the structure

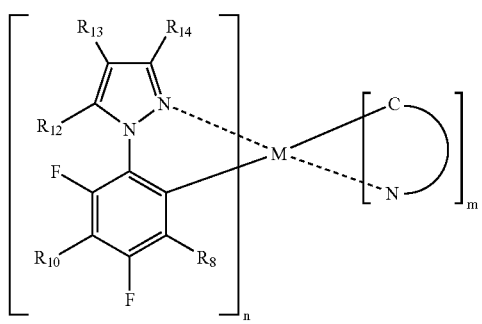

wherein
M is a metal having an atomic weight greater than 40;
(C—N) is a substituted or unsubstituted cyclometallated ligand, and (C—N) is different from at least one other ligand attached to the metal;
each $R_8$, $R_{10}$, and $R_{12}$ to $R_{14}$ is independently selected from hydrogen, alkyl, alkenyl, alkynyl, alkylaryl, CN, $CF_3$, $NO_2$, halo, aryl, heteroaryl, substituted aryl, substituted heteroaryl, or a heterocyclic group;
additionally or alternatively, any two adjacent substituted positions together form, independently, a fused 4- to 7-member cyclic group, wherein said cyclic group is cycloalkyl, cycloheteroalkyl, aryl, or heteroaryl, and wherein the 4- to 7-member cyclic group may be optionally substituted with a substituent independently selected from hydrogen, alkyl, alkenyl, alkynyl, alkylaryl, CN, $CF_3$, $NO_2$, halo, aryl, heteroaryl, substituted aryl, substituted heteroaryl, or a heterocyclic group;
m has a value of at least 1;
n has a value of at least 1; and
m+n is the maximum number of ligands that may be attached to the metal.

29. The device of claim 28, wherein n is 2.

30. The device of claim 29, wherein each ligand is organometallic.

31. The device of clam 28, wherein M is selected from the group consisting of Ir, Pt, Pd, Rh, Re, Ru, Os, Tl, Pb, Bi, In, Sn, Sb, Te, Au, or Ag.

32. The device of claim 31, wherein M is Ir.

33. The device of claim 28, wherein at least one of $R_8$, $R_{10}$, $R_{12}$ to $R_{14}$, and a substituent of (C—N) is independently selected from substituted or unsubstituted phenyl, napthyl, or pyridyl.

34. The device of claim 33, wherein at least one of $R_8$, $R_{10}$, $R_{12}$ to $R_{14}$, and a substituent of (C—N) is phenyl.

35. The device of claim 34, wherein the compound has a structure selected from the group consisting of:

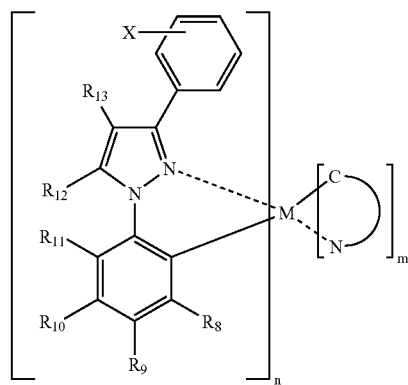

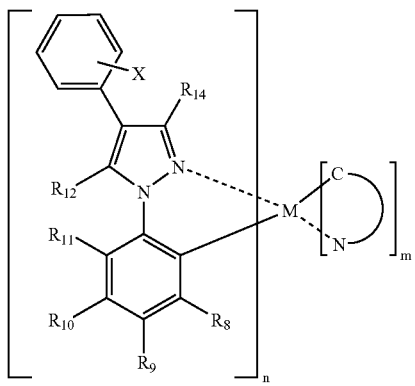

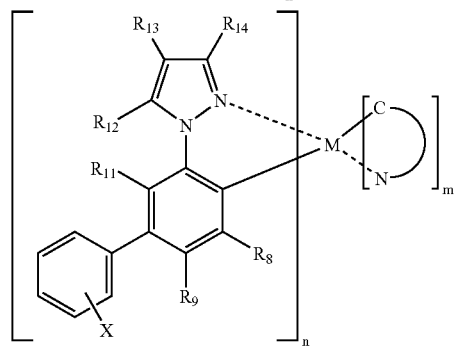

-continued

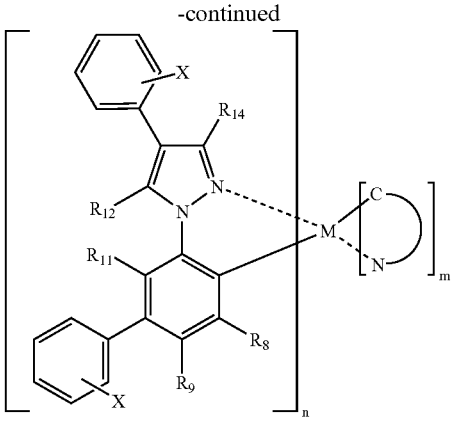

wherein X is independently selected from hydrogen, alkyl, alkenyl, alkynyl, alkylaryl, CN, $CF_3$, $NO_2$, halo, aryl, heteroaryl, substituted aryl, substituted heteroaryl, or a heterocyclic group;

additionally or alternatively, any two adjacent substituted positions together form, independently, a fused 4- to 7-member cyclic group, wherein said cyclic group is cycloalkyl, cycloheteroalkyl, aryl, or heteroaryl, and wherein the 4- to 7-member cyclic group may be further substituted by substituent X; and $R_9$ and $R_{11}$ are F.

36. The device of claim 28, wherein the compound has a structure selected from the group consisting of:

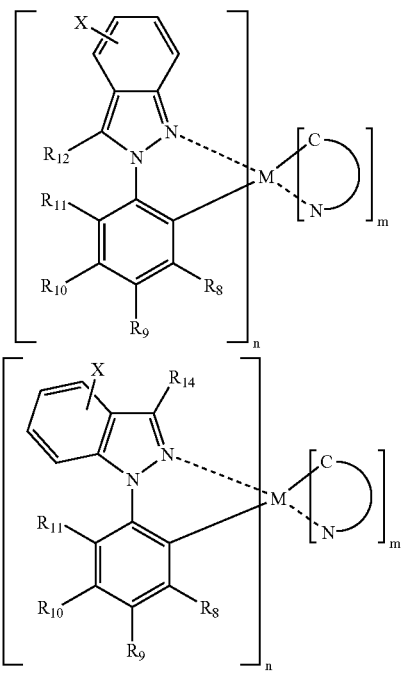

wherein X is independently selected from hydrogen, alkyl, alkenyl, alkynyl, alkylaryl, CN, $CF_3$, $NO_2$, halo, aryl, heteroaryl, substituted aryl, substituted heteroaryl, or a heterocyclic group;

additionally or alternatively, any two adjacent substituted positions together form, independently, a fused 4- to 7-member cyclic group, wherein said cyclic group is cycloalkyl, cycloheteroalkyl, aryl, or heteroaryl, and wherein the 4- to 7-member cyclic group may be further substituted by substituent X; and $R_9$ and $R_{11}$ are F.

37. The device of claim 28, wherein the compound has a structure selected from the group consisting of:

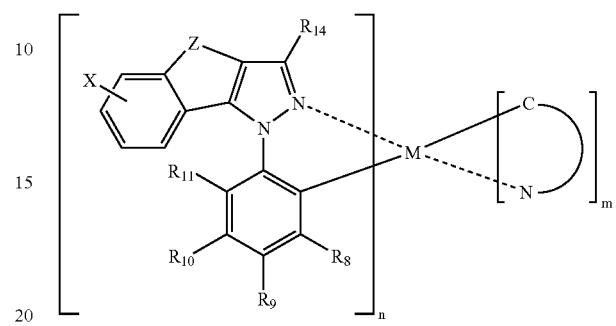

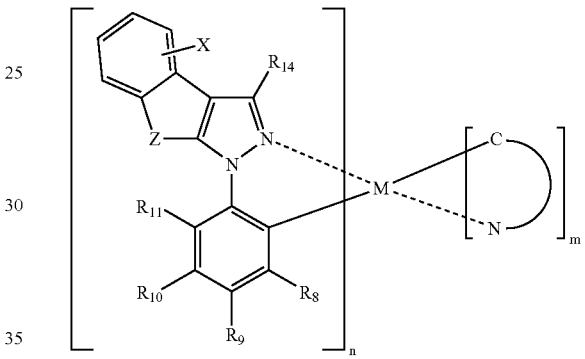

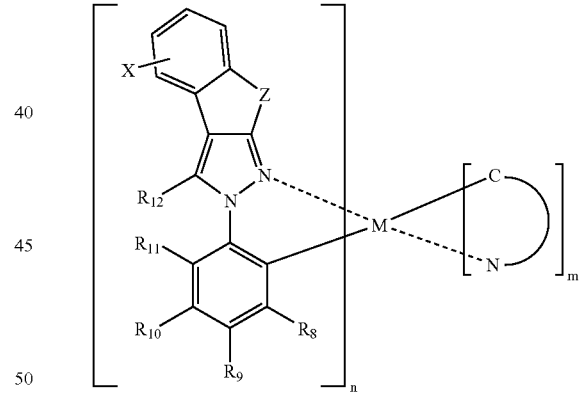

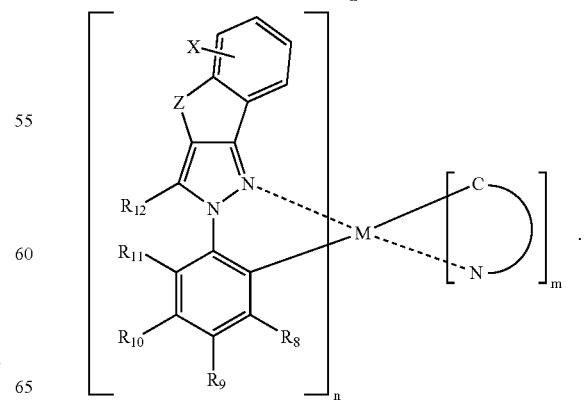

wherein X is independently selected from hydrogen, alkyl, alkenyl, alkynyl, alkylaryl, CN, CF$_3$, NO$_2$, halo, aryl, heteroaryl, substituted aryl, substituted heteroaryl, or a heterocyclic group;

additionally or alternatively, any two adjacent substituted positions together form, independently, a fused 4- to 7-member cyclic group, wherein said cyclic group is cycloalkyl, cycloheteroalkyl, aryl, or heteroaryl, and wherein the 4- to 7-member cyclic group may be further substituted by substituent X;

Z is selected from —CH$_2$, —CRR, —NH, —NR, —O, —S, —SiR wherein R is independently selected from hydrogen, alkyl, alkenyl, alkynyl, alkylaryl, CN, CF$_3$, NO$_2$, halo, aryl, heteroaryl, substituted aryl, substituted heteroaryl, or a heterocyclic group; and R$_9$ and R$_{11}$ are F.

38. The device of claim 28, wherein the compound is a phosphorescent emissive material.

39. The device of claim 28, wherein at least one ligand is a phosphorescent emissive ligand in the compound at room temperature and at least one ligand is not a phosphorescent emissive ligand at room temperature.

40. The device of claim 39, wherein the ligand emissive in at room temperature in the compound has a triplet energy corresponding to a wavelength that is at least 80 nm greater than the wavelength corresponding to the triplet energy of the ligand that is not emissive in the compound at room temperature.

41. The device of claim 40, wherein the emissive ligand is organometallic.

42. The device of claim 40, wherein the emissive ligand has a triplet energy corresponding to a wavelength of 500-520 nm.

43. The device of claim 40, wherein the emissive ligand has a triplet energy corresponding to a wavelength greater than 590 nm.

44. The organic light emitting device of claim 40, wherein each ligand is organometallic.

45. The device of claim 44, wherein the emissive ligand has a triplet energy corresponding to a wavelength of 500-520 nm.

46. The device of claim 44, wherein the emissive ligand has a triplet energy corresponding to a wavelength greater than 590 nm.

47. The device of claim 44, wherein the device is incorporated into a consumer product.

48. An organic light emitting device, comprising:
(a) an anode;
(b) a cathode; and
(c) an emissive layer disposed between and electrically connected to the anode and the cathode, the emissive layer further comprising a compound having the structure

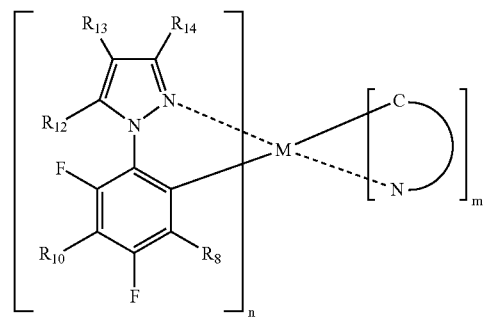

wherein

M is Ir;

(C—N) is a substituted or unsubstituted cyclometallated ligand, and (C—N) is different from at least one other ligand attached to the metal;
each R$_8$, R$_{10}$, and R$_{12}$ to R$_{14}$ are H;
m has a value of at least 1;
n has a value of at least 1; and
m+n is the maximum number of ligands that may be attached to the metal.

49. The device of claim 48, wherein n is 2 and m is 1.

50. The device of claim 49, wherein the compound has the structure:

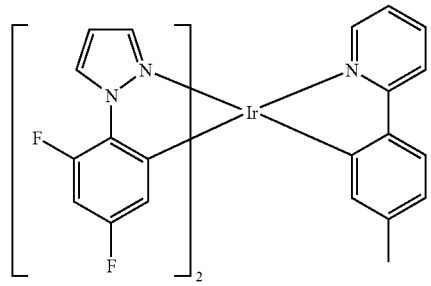

51. The device of claim 49, wherein the compound has the structure:

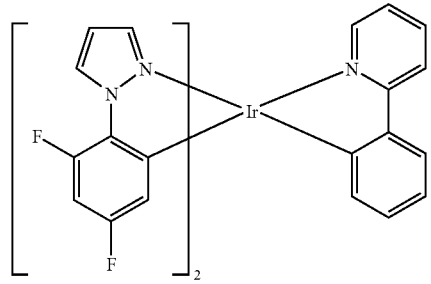

52. The device of claim 49, wherein the compound has the structure:
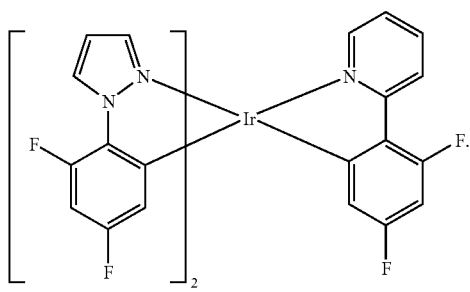
53. The device of claim 49, wherein the compound has the structure:
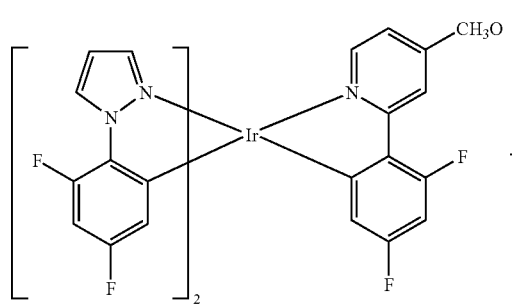
54. The device of claim 49, wherein the compound has the structure:
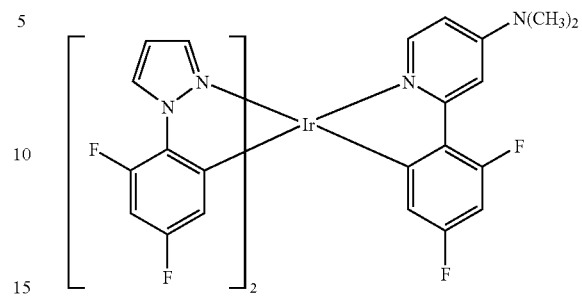
55. The device of claim 49, wherein the compound has the structure:
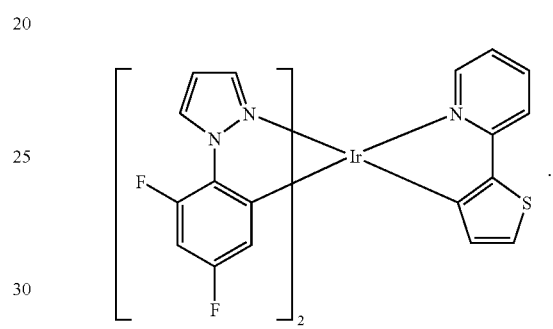
* * * * *